US007753849B2

(12) United States Patent
Morgan et al.

(10) Patent No.: US 7,753,849 B2
(45) Date of Patent: Jul. 13, 2010

(54) DOPPLER RADAR CARDIOPULMONARY SENSOR AND SIGNAL PROCESSING SYSTEM AND METHOD FOR USE THEREWITH

(75) Inventors: Dennis R. Morgan, Morristown, NJ (US); Michael G. Zierdt, Hillsborough, NJ (US)

(73) Assignee: Alcatel-Lucent USA Inc., Murray Hill, NJ (US)

( * ) Notice: Subject to any disclaimer, the term of this patent is extended or adjusted under 35 U.S.C. 154(b) by 0 days.

(21) Appl. No.: 12/117,947

(22) Filed: May 9, 2008

(65) Prior Publication Data

US 2009/0278728 A1  Nov. 12, 2009

(51) Int. Cl.
*B65D 81/00* (2006.01)
(52) U.S. Cl. .................. 600/453; 600/455; 600/457
(58) Field of Classification Search .......... 600/453, 600/454, 455, 457
See application file for complete search history.

(56) References Cited

U.S. PATENT DOCUMENTS

2004/0129064 A1* 7/2004 Hinterdorfer et al. ......... 73/105
2008/0074307 A1* 3/2008 Boric-Lubecke et al. ...... 342/28

OTHER PUBLICATIONS

James C. Lin "Noninvasive Microwave Measurement of Respiration" Proceedings of the IEEE, p. 1530, Oct. 1975.
P.C. Pedersen, et al., "An Investigation of the Use of MIcrowave Radiation for Pulmonary Diagnostics" IEEE Transactions on Biomedical Engineering, pp. 410-412, Sep. 1976.
Donald W. Griffin "MW Interferometers for Biological Studies" Microwave Journal, vol. 21, No. 5, pp. 69-72, May 1978.
James C. Lin, et al., "Microwave Apexcardiography" IEEE Transactions on Microwave Theory and Techniques, vol. MTT-27, No. 6, pp. 618-620, Jun. 1979.
Kun-Mu Chen, et al., "An X-Band Microwave Life-Detection System" IEEE Transactions on Biomedical Engineering, vol. BME-33, No. 7, pp. 697-701, Jul. 1986.
Amy Droitcour, et al., "A Microwave Radio for Doppler Radar Sensing of Vital Signs" IEEE MTT-S Digest, pp. 175-178, 2001.
B. Lohman, et al., "A Digital Signal Processor for Doppler Radar Sensing of Vital Signs" Proceedings of the 23rd Annual EMBS International Conference, Istanbul, Turkey, pp. 3359-3362, Oct. 25-28, 2001.
O. Boric Lubecke, et al., "10 GHz Doppler Radar Sensing of Respiration and Heart Movement" Proc. IEEE 28th Annual Northeast Bioengineering Conf., pp. 55-56, 2002.

(Continued)

*Primary Examiner*—Thomas H Tarcza
*Assistant Examiner*—Timothy A Brainard
(74) *Attorney, Agent, or Firm*—Hitt Gaines, PC

(57) ABSTRACT

A Doppler radar signal processing system and method and a Doppler radar employing the system or the method. In one embodiment, the system includes: (1) an input configured to receive at least one radar output signal representing a reflected Doppler radar signal, (2) signal processing circuitry coupled to the input and configured to produce an arc-length cardiopulmonary signal from the at least one radar output signal and employ a respiration fundamental frequency estimate to extract a heart rate signal from the arc-length cardiopulmonary signal and (3) an output coupled to the signal processing circuitry and configured to provide the heart rate signal.

20 Claims, 32 Drawing Sheets

OTHER PUBLICATIONS

Amy D. Droitcour, et al., "Range Correlation Effect on ISM Band I/Q CMOS Radar for Non-Contact Vital Signs Sensing" IEEE MTT-S Digest, pp. 1945-1948, 2003.

Amy D. Droitcour, et al., "Range Correlation and I/Q Performance Benefits in Single-Chip Silicon Doppler Radars for Noncontact Cardiopulmonary Monitoring" IEEE Transactions on Microwave Theory and Techniques, vol. 52, No. 3, pp. 838-848, Mar. 2004.

Olga Boric-Lubecke, et al., "Doppler Radar Sensing of Multiple Subjects in Single and Multiple Antenna Systems" Proc. 7th Int. Conf. Telecommunications in Modern Satellite, Cable, Broadcasting Services, vol. 1, pp. 7-11, Sep. 28-30, 2005.

Dragan Samardzija, et al., "Applications of MIMO Techniques to Sensing of Cardiopulmonary Activity" Proc. IEEE/ACES Int. Conf. Wireless Communications, Applied Computational Electromagnetics, pp. 618-621, 2005.

Qin Zhou, et al., "Detection of Multiple Heartbeats Using Doppler Radar" Proc. IEEE Int. Conf. Acoustics, Speech, Signal Processing (ICCASSP), vol. 2, pp. II-1160-II-1163, 2006.

Amy D. Droitcour "Non-Contact Measurement of Heart and Respiration Rates with a Single-Chip Microwave Doppler Radar" Ph.D. Dissertation, Stanford University, Jun. 2006.

G. Ramachandran, et al., "Reconstruction of Out-of-Plane Cardiac Displacement Patterns as Observed on the Chest Wall During Various Phases of ECG by Capacitance Transducer" IEEE Transactions on Biomedical Engineering, vol. 38, No. 4, pp. 383-385, Apr. 1991.

Petre Stoica, et al., "Introduction to Spectral Analysis" Upper Saddle River, New Jersey, Prentice Hall, Chapter 2, 1997.

\* cited by examiner

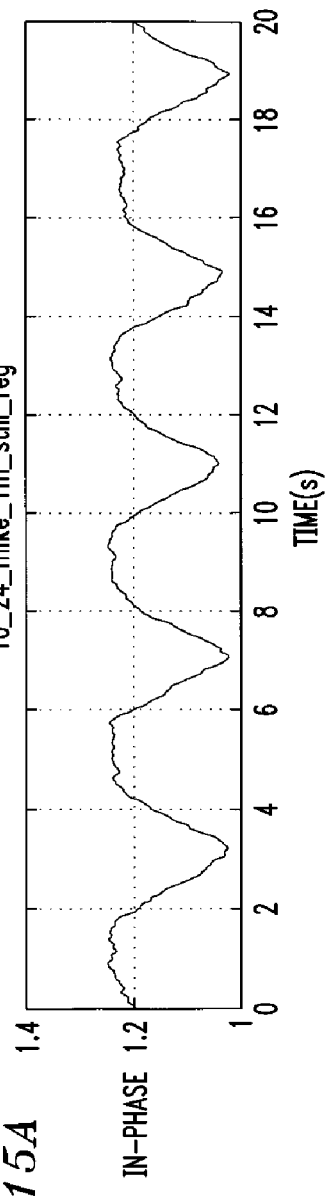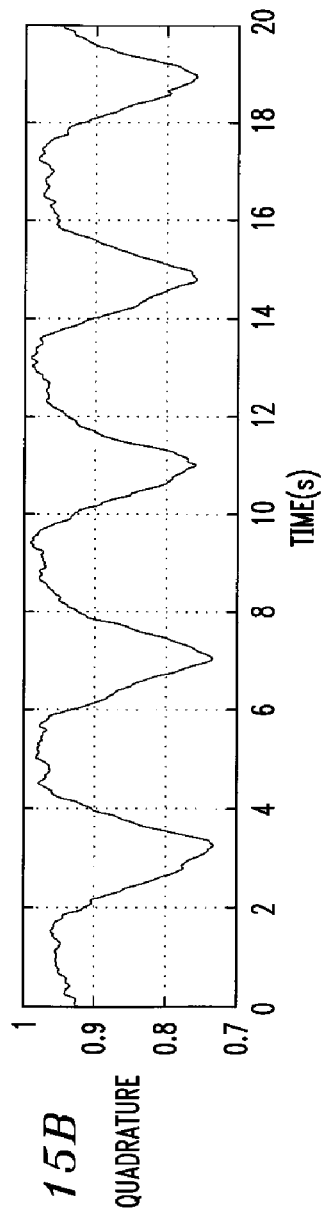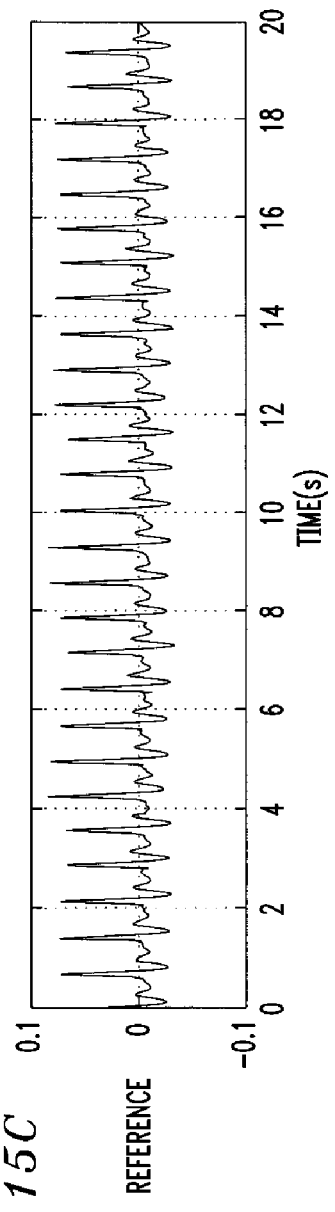
FIG. 15A
FIG. 15B
FIG. 15C

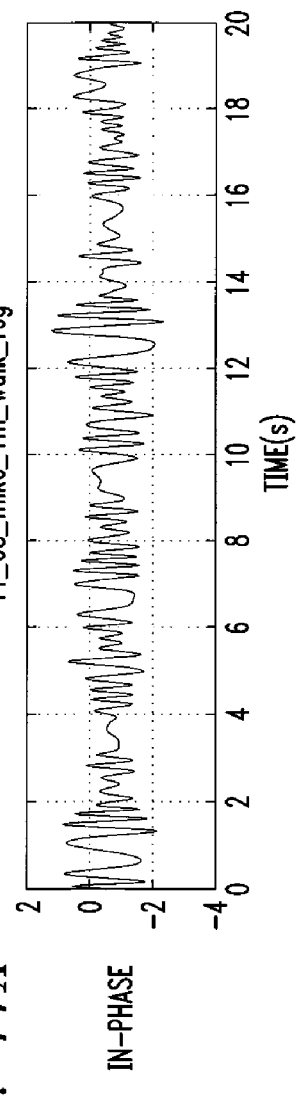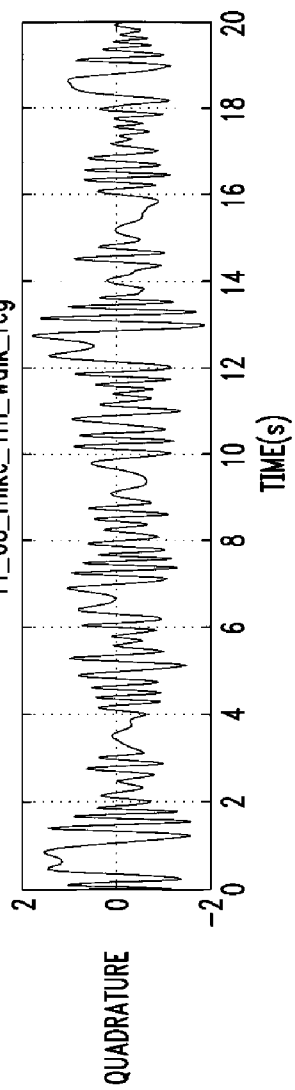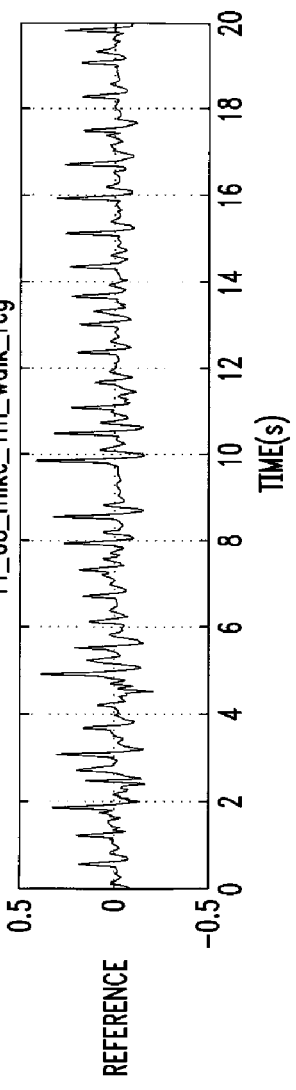
FIG. 17A IN-PHASE
FIG. 17B QUADRATURE
FIG. 17C REFERENCE

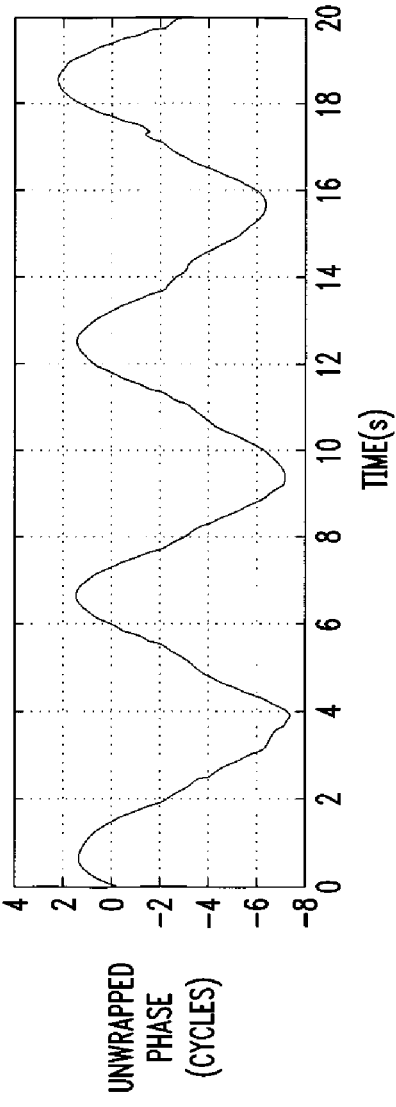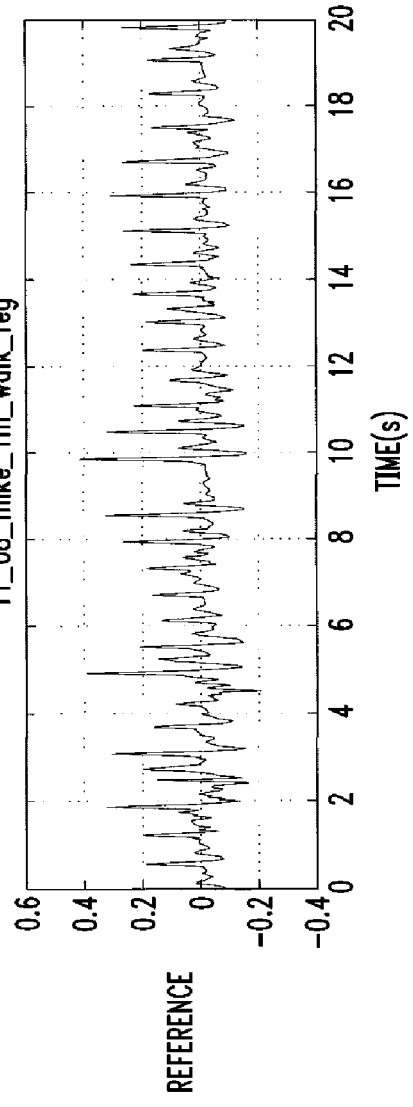
FIG. 17D
FIG. 17E

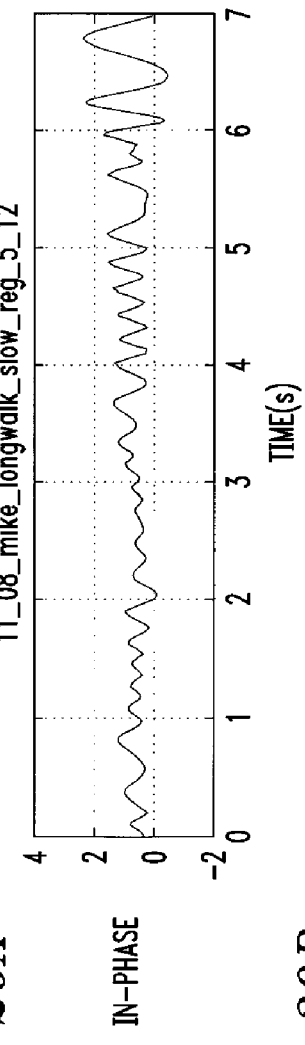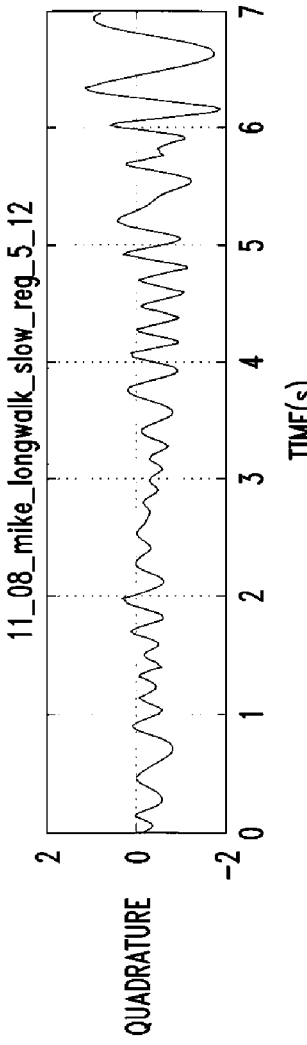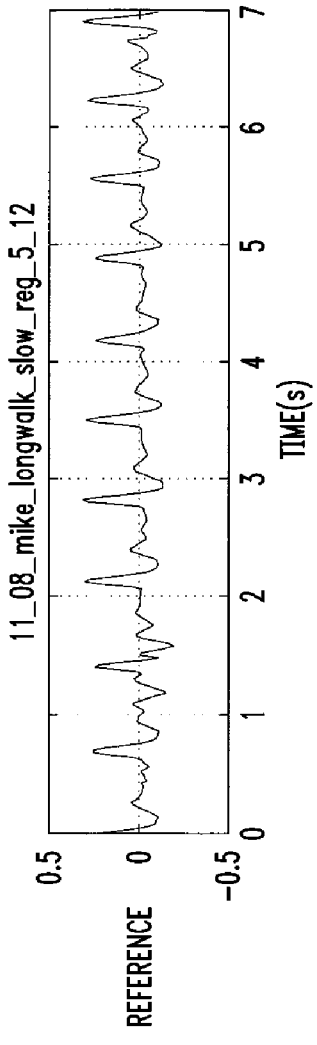
FIG. 20A  IN-PHASE
FIG. 20B  QUADRATURE
FIG. 20C  REFERENCE

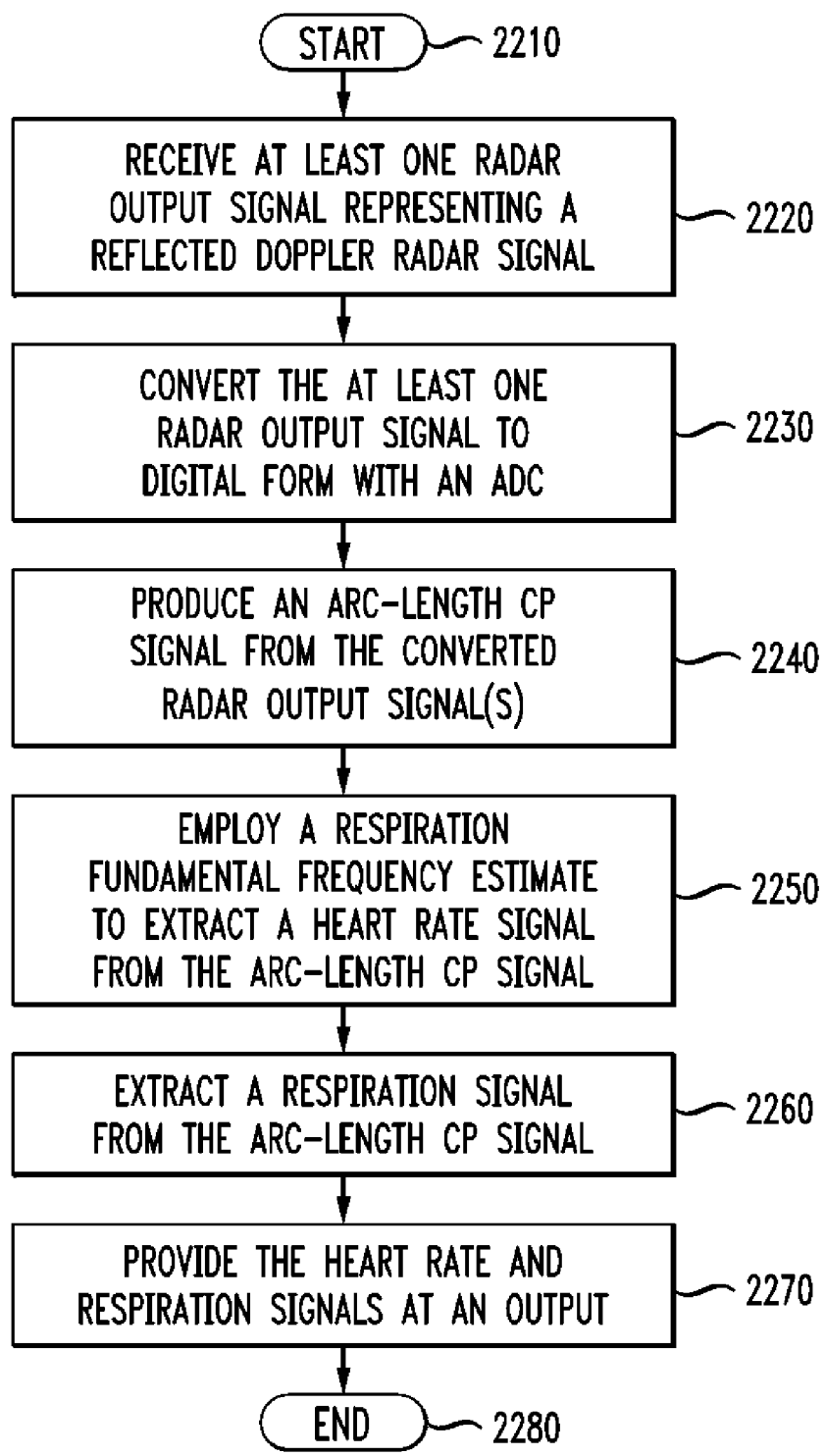

DOPPLER RADAR CARDIOPULMONARY SENSOR AND SIGNAL PROCESSING SYSTEM AND METHOD FOR USE THEREWITH

TECHNICAL FIELD OF THE INVENTION

The invention is directed, in general, to signal processing and, more specifically, to a Doppler radar cardiopulmonary (CP) sensor and signal processing system and method for use therewith.

BACKGROUND OF THE INVENTION

This section introduces aspects that may help facilitate a better understanding of the invention. Accordingly, the statements of this Background of the Invention section are to be read in this light and are not to be understood as admissions about what is, or what is not, prior art.

Many potential applications exist for a non-invasive technique to monitor respiration, heartbeat or both. Doppler radar, operating at microwave frequencies in the range of 1-10 GHz, has long been suggested as a means to accomplish this (see, e.g., Lin, "Noninvasive Microwave Measurement of Respiration," Proc. IEEE, vol. 63, p. 1530, October 1975; Pedersen, et al., "An Investigation of the employ of Microwave Radiation for Pulmonary Diagnostics," IEEE Trans. Biomed. Eng, vol. BME-23, pp. 410-412, September 1976; Griffin, "MW Interferometers for Biological Studies," Microw. J., vol. 21, pp. 69-72, May 1978; Lin, et al., "Microwave Apexcardiography," IEEE Trans. Microw. Theory Tech., vol. MTT-27, pp. 618-620, June 1979; and Chen, et al., "An X-band Microwave Life-Detections System," IEEE Trans. Biomed. Eng., vol. BME-33, pp. 697-701, July 1986).

More recently, radio frequency (RF) technology developed for mobile telephones (i.e., cellphones) has been applied to implement such devices (see, e.g., Droitcour, et al., "A Microwave Radio for Doppler Radar Sensing of Vital Signs," in IEEE MTT-S Int. Microwave Symp. Dig., 2001, vol. 1, pp. 175-178; Lohman, et al., "A Digital Signal Processor for Doppler Radar Sensing of Vital Signs," in Proc. IEEE 23rd Annual Engineering in Medicine and Biology Soc. Conf., 2001, vol. 4, pp. 3359-3362; Boric-Lubecke, et al., "10 GHz Doppler Sensing of Respiration and Heart Movement," in Proc. IEEE 28th Annual Northeast Bioengineering Conf., 2002, pp. 55-56; Droitcour, et al., "Range Correlation Effect on ISM Band I/Q CMOS Radar for Non-contact Vital Signs Sensing," in IEEE MTT-S Int. Microwave Symp. Dig., 2003, vol. 3, pp. 1945-1948; and Droitcour, et al., "Range correlation and I/Q performance benefits in Single-Chip Silicon Doppler Radars for Noncontact Cardiopulmonary Monitoring," IEEE Trans. Microw. Theory Tech., vol. 52, pp. 838-848, March 2004).

Mobile telephone RF technology has also been generalized to sensing of multiple subjects (see, e.g., Boric-Lubecke, et al., "Doppler Radar Sensing of Multiple Subjects in Single and Multiple Antenna Systems," in Proc. 7th Int. Conf. Telecommunications in Modern Satellite, Cable, Broadcasting Services, 2005, vol. 1, pp. 7-11; Smardzija, et al., "Applications of MIMO Techniques to Sensing of Cardiopulmonary Activity," in Proc. IEEE/ACES Int. Conf. Wireless Communications, Applied Computational Electromagnetics, 2005, pp. 618-621; and Zhou, et al., "Detection of Multiple Heartbeats Using Doppler Radar," in Proc. IEEE Int. Conf. Acoustics, Speech, Signal Processing (ICASSP), 2006, vol. 2, pp. II-1160-11-1163). A particularly comprehensive discourse on the subject including physiological background can be found in Droitcour, Non-Contact Measurement of Heart and Respiration Rates with a Single-Chip Microwave Doppler Radar, Ph.D. Dissertation, Stanford University, 2006.

Most of the studies to date have been done in the form of laboratory experiments under ideal conditions, so substantial concern exists that the technology can ever be developed into reliable products. Some potential problems that have yet to be addressed include the effects of background scatter, the motion of the subject as well as the background and interference between the respiration and heartbeat signals. Background scatter both from the ambient surroundings as well as from parts of the subject's body exclusive of the relevant chest-wall area (see, e.g., Ramachandran, et al., "Reconstruction of Out-Of-Plane Cardiac Displacement Patterns as Observed on the Chest Wall During Various Phases of ECG by Capacitance Transducer," IEEE Trans. Biomed. Eng., vol. BME-38, pp. 383-385, April 1991) adds a component to the desired signal that must be dealt with. Gross motion of the subject, as well as other objects in the background will introduce undesired dynamics into the desired signal, making the problem even more difficult. Finally, the problem remains of respiration harmonics falling close to the heartbeat frequency so as to make reliable heart rate estimation difficult. What is needed in the art is a way to overcome these problems. More specifically, what is needed in the art are CP signal processing systems and methods that ameliorate some or all of the above-described disruptive effects and an improved Doppler radar that takes advantage of the systems and methods.

SUMMARY OF THE INVENTION

To address the above-described deficiencies of the prior art, the invention provides a Doppler radar signal processing system. In one embodiment, the system includes: (1) an input configured to receive at least one radar output signal representing a reflected Doppler radar signal, (2) signal processing circuitry coupled to the input and configured to produce an arc-length cardiopulmonary signal from the at least one radar output signal and employ a respiration fundamental frequency estimate to extract a heart rate signal from the arc-length cardiopulmonary signal and (3) an output coupled to the signal processing circuitry and configured to provide the heart rate signal.

Another aspect of the invention provides a method of CP signal processing. In one embodiment, the method includes: (1) receiving at least one radar output signal representing a reflected Doppler radar signal, (2) producing an arc-length cardiopulmonary signal from the at least one radar output signal, (3) employing a respiration fundamental frequency estimate to extract a heart rate signal from the arc-length cardiopulmonary signal and (4) providing the heart rate signal at an output.

Yet another aspect of the invention provides a Doppler radar. In one embodiment, the Doppler radar includes: (1) Doppler radar circuitry configured to transmit a Doppler radar signal, receive and demodulate a reflected Doppler radar signal and produce in-phase and quadrature radar output signals representing the reflected Doppler radar signal, (2) signal processing circuitry coupled to the input and configured to produce an arc-length cardiopulmonary signal from the in-phase and quadrature radar output signals and employ a respiration fundamental frequency estimate to extract a heart rate signal from the arc-length cardiopulmonary signal and (3) an output coupled to the signal processing circuitry and configured to provide the heart rate signal.

BRIEF DESCRIPTION OF THE DRAWINGS

For a more complete understanding of the invention, reference is now made to the following descriptions taken in conjunction with the accompanying drawings, in which:

FIGS. 15A-C are plots of a raw I signal (FIG. 15A), a raw Q signal (FIG. 15B) and a reference signal (FIG. 15C) for Experiment 2 under three conditions: subject stationary at 1 m from antenna, remaining still and breathing regularly;

FIGS. 17A-C are plots of a raw I signal (FIG. 17A), a raw Q signal (FIG. 17B) and a reference signal (FIG. 17C) for Experiment 3 under three conditions: subject reciprocating at 1 m from antenna and breathing regularly;

FIG. 17D is a plot of the unwrapped phase arctangent of the I and Q signals of FIGS. 17A and 17B;

FIG. 17E is a plot of the arc length signal relating to the reference signal of FIG. 17C;

FIGS. 20A-C are plots of 5-s to 12-s windows of the respective raw I, Q and reference signals of FIGS. 19A-C;

FIG. 22 is a flow diagram of one embodiment of a method of CP signal processing.

DETAILED DESCRIPTION

I. Introduction

Disclosed herein are various signal processing systems and methods for Doppler radar CP sensing. These systems and methods enable independent recovery of respiration and heartbeat signals from measurements of chest-wall dynamic motion, which may then be employed to generate independent respiration and heart rate estimates. A generic model in the complex plane will be formulated to visualize production of the desired chest-wall displacement signal along with various interfering signals. From this, systems and methods will be derived for arc length demodulation and cardio/pulmonary separation. A test generator is developed to simulate actual signals. Also, an experimental setup is presented and several sets of real data are analyzed using the new signal processing techniques.

Section II, below, develops a physical model of the signal and propagation scenario to set the stage for a description of signal processing systems and methods. Then Section III describes some signal processing systems and method embodiments, including prefiltering and analog-to-digital conversion, raw CP signal extraction and spectral analysis. Section IV introduces a technique for mitigating heartbeat signal interference from the respiratory component. Section V introduces simulation techniques, particularly including a test signal to represent chest-wall motion which may be employed to demonstrate the signal processing systems and methods. Section VI validates and extends the simulation results using experimental data collected with a real RF Doppler radar system using a live subject.

Figure 1:
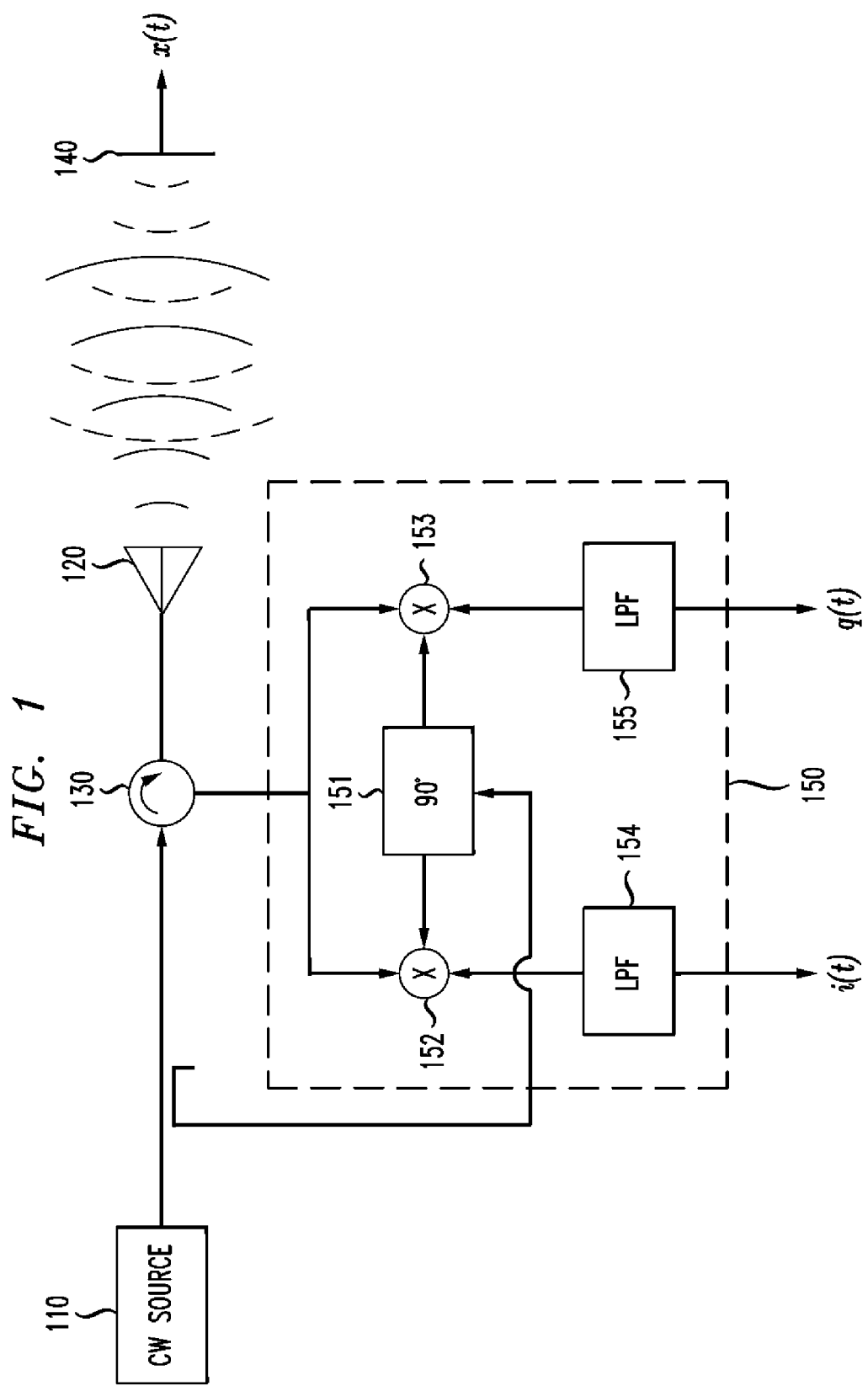
FIG. 1 is a block diagram of one embodiment of a Doppler radar with which a CP signal processing system or method may be contained or carried out.

FIG. 1 shows a block diagram of a conventional Doppler radar. A continuous-wave (CW) source 110 feeds an antenna 120 through a circulator 130. The antenna 120 radiates to a desired object 140 in a field of view (not referenced) that experiences motion x(t). The object 140 reflects the signal back to the same antenna 120. In an alternative embodiment, the object 140 reflects the signal to another antenna (not shown).

The circulator 130 then captures the reflected Doppler radar signal and directs it to a demodulator 150. The demodulator 150 uses a portion of the CW source signal to demodulate the reflected Doppler radar signal. In one embodiment, the demodulator 150 produces a single output signal. However, in the illustrated embodiment, the demodulator 150 is an I/Q (complex) demodulator 150. The I/Q demodulator takes a portion of the CW source signal, splits it into two components with 90° relative phase shifter 151, and mixes it with the reflected signal in respective mixers 152, 153 to derive in-phase and quadrature (I/Q) outputs, i(t) and q(t), respectively. In the illustrated embodiment, lowpass filters (LPFs) 154, 155 are employed to remove images and retain only signals that are changing relatively slowly compared to the CW source signal frequency.

As the scattering object moves, the phase of the return signal varies as $$\frac{2\pi x(t)}{\frac{\lambda}{2}}, \text{ where } \lambda = \frac{c}{f_c}$$

is the wavelength of the CW signal, c is the velocity of light, and $f_c$ is the CW carrier frequency. (The divisor of 2 on $\lambda$ is due to the two-way propagation path to and from the scatterer.) Therefore, as the scattering object moves radially, the phase rotates 360° every $$\frac{\lambda}{2}.$$

For example, if $f_c$=2.4 GHz, then the wavelength is approximately ⅛ m or 12.5 cm for c=3×10⁸ m/s and the phase rotates 360° for every 6.25 cm of motion.

II. Signal Model

Figure 2A:
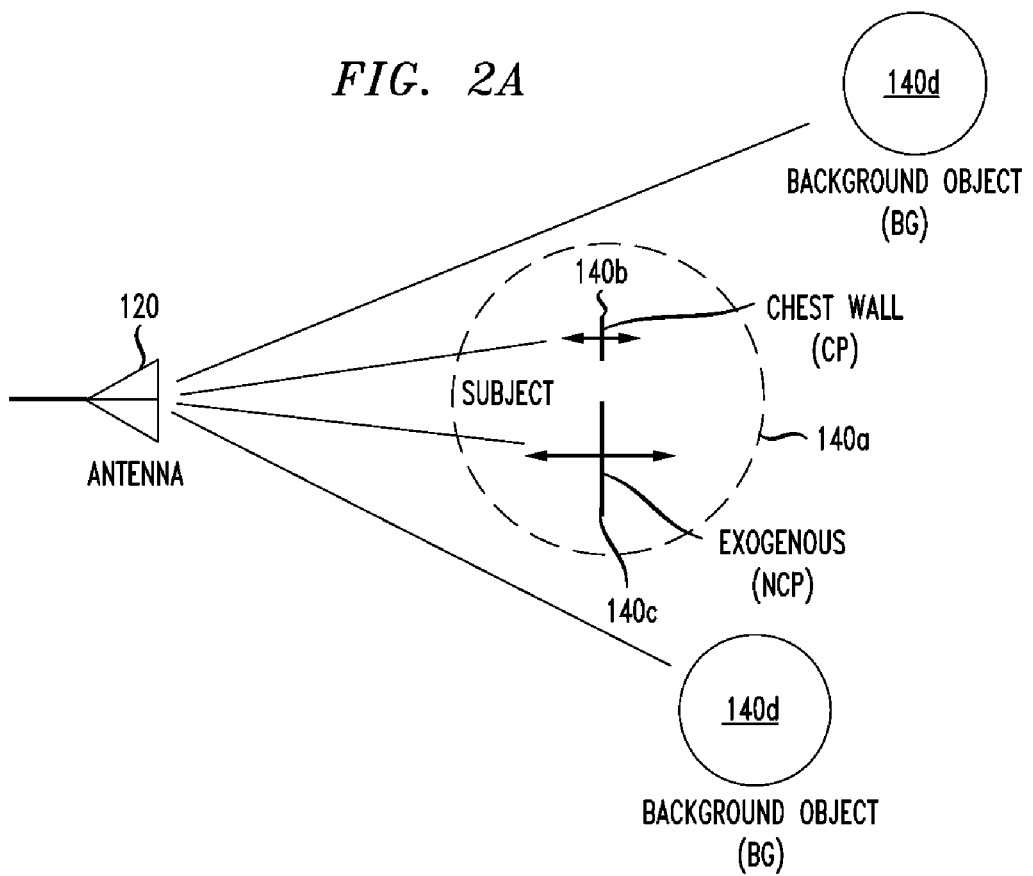
FIG. 2A is a schematic geometrical diagram showing an example of propagation that may occur with respect to the Doppler radar of FIG. 1.

FIG. 2A shows a schematic geometrical diagram of the propagation scenario. The desired backscattered signal comes from objects (140 of FIG. 1) in the field of view, including a subject 140a. A chest-wall area 140b of the subject 140a produces the desired component. Undesired interfering components often arise from other backscattering areas on the subject (e.g., 140c), as well as from other background objects in the antenna field of view, e.g., objects 140d. An antenna with a narrow beam pattern (i.e., a high gain) can significantly reduce interference from background objects 140d, although the desired subject is restricted to a smaller area, since he should remain in the beam at all times. Also, for many applications, it is probably not feasible to employ the antenna pattern to exclude undesired returns from subject areas outside of the chest wall. Accordingly, for purposes of the present description, two subject backscatter components are defined: CP and non-CP (NCP). All other backscatter is defined as a background (BG) component, including backscatter from walls, ceilings or other objects within the field of view.

Figure 2B:
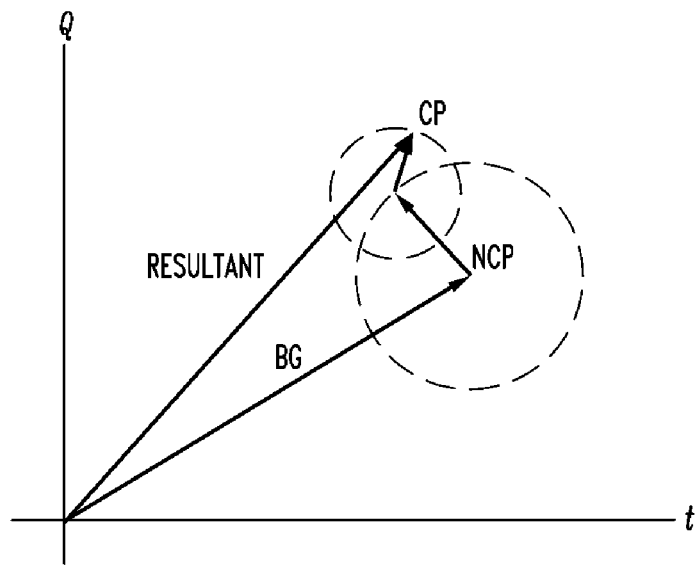
FIG. 2B is a phasor diagram showing received backscatter that the Doppler radar of FIG. 1 may encounter.

Turning to FIG. 2B, the return from each backscattering object within the antenna field of view can be visualized as a vector in a complex plane, where its length is proportional to the reflection coefficient, and its orientation represents the RF phase, which as previously described varies with radial distance. The various CP, NCP, and BG components described and defined above are then added in this vector space as shown in FIG. 2B, where the resultant vector represents the composite return from all scatterers. In this diagram, the BG component is presumed stationary, but the position of the CP and NCP subject components can lie anywhere along the dashed circle loci. As the subject moves, either voluntarily or involuntarily, the NCP component will wander along an arc of its locus. On the other hand, the motion of the desired CP component will be relatively much smaller, since chest-wall movement due to respiration is only a centimeter or so at most and the motion due heartbeat is typically only a fraction of a millimeter (see, e.g., Droitcour, Non-Contact Measurement supra). Therefore, the CP component will only vary over a small arc, which for all practical purposes can be considered as a straight line.

III. Basic Signal Processing

A. Prefiltering and Analog-to-Digital Conversion

In a digital embodiment (which is preferred for many applications), it is necessary to digitize the I/Q analog output signals of the complex demodulator 150 of FIG. 1. Since the CP component, shown as the small arc in FIG. 2B, is of primary interest, it might at first seem best to AC-couple, or highpass-filter, the analog outputs to the analog-to-digital converters (ADCs), to reduce the dynamic range requirements and number of bits needed for accurate representation. Furthermore, the cutoff frequency of the highpass filter could be made high enough to exclude most of the respiration signal, thereby enhancing the much smaller, and more elusive, heartbeat signal. However, AC coupling has two disadvantages: a long settling time and a loss of possibly useful DC and low-frequency information, as described below.

It is envisaged that CP data for a given subject under given conditions will be acquired over a time frame on the order of 5-30 s for most applications. If AC coupling is employed, some time must be allotted for the filter to settle after the subject is in position and ready to begin the test. The settling time of a highpass filter is roughly the inverse of its cutoff frequency. The respiration rate for a seated subject at rest is typically in the range of 5-20 breaths per minute (bpm), i.e., 0.083-0.33 Hz. Therefore, with a cutoff frequency of 0.03 Hz, the settling time will be on the order of 30 seconds, which is long compared to the envisaged time frames for valid data acquisition. Increasing the cutoff frequency can reduce this settling time, but at the expense of losing some of the low-frequency information, as described next.

It will be shown herein that harmonics of the fundamental respiration frequency can seriously limit heart-rate estimation accuracy. As will be described below in Section IV, various ways of dealing with this interference require an estimate of the respiration rate. Therefore, the highpass cutoff should be set below the lowest expected respiration frequency, thereby increasing the settling time, as described above. Another reason that low-frequency data might be useful is for applications in which the actual respiration waveform might be diagnostically useful.

Another consideration for the prefiltering is the lowpass anti-aliasing filter required. Heart rate for a seated subject at rest is typically in the range of 45-90 beats per minute (bpm), i.e., 0.75-1.5 Hz. Also, within a heartbeat period, fine detail exists that may be of diagnostic value, so that frequencies of 10-100 times the highest heartbeat frequency may be of interest. Therefore, the lowpass cutoff frequency should be on the order of 15-150 Hz, requiring sampling rates in the range 30-300 Hz. Various experiments described below employ sampling rates of 25 Hz and 50 Hz. With activity, such as on a treadmill, heart rate can easily increase to 120 bpm (2 Hz) (An oft-cited rule of thumb for maximum heart rate is 220 minus the subject's age in years.) Some applications may require a somewhat higher sampling rate.

For all of the above reasons, DC coupling to the ADC appears preferable to AC coupling. However, both fall within the scope of the invention. The DC can still be removed after collection by subtracting out the mean over the data block. In steady state, this is equivalent to highpass filtering with a very low cutoff frequency. However, subtracting out the mean after collection avoids the transient settling time problem.

The penalty paid for DC coupling is that the ADC then requires more bits because of the vastly increased dynamic range. However, considering the relatively low sampling rates, the requirements are readily achievable with today's technology. Indeed, commercially available 24-bit ADCs are available at relatively modest cost and small size. Moreover, if the background (140*d* of FIG. 2A) is immobile, then the BG component in FIG. 2B is a DC component that can be offset prior to the ADC to reduce some of the dynamic range.

B. Extraction of Raw CP Signal

Ideally, a DC offset should be employed to reference the data to the center of the smaller dashed circle (CP) in FIG. 2B. Then the desired chest-wall displacement signal (shown as x(t) in FIG. 1) could be reconstructed by merely taking the arctangent of the complex I/Q data. It is possible and desirable to offset the DC corresponding to the BG return in FIG. 2A, assuming that the constituent scattering objects are not moving. However, it is difficult to avoid the NCP component, which is induced as a result of voluntary or involuntary body movement. Since the NCP component is unpredictable, the focus should be on the small CP arc, which contains the signal of interest.

If the subject is moving at a steady velocity, the sum of the CP and NCP vectors in FIG. 2B rotates about the center of the larger dashed circle, i.e., the head of the presumably static BG vector. As the subject moves in this manner, the CP and NCP components maintain a rough alignment, because the chest wall nominally moves with the rest of the body. However, some angular motion of one exists with respect to the other because of relative local motion and, of course, the actual desired CP motion of the chest wall. As will be shown in the experiments below, the CP signal may not always be able to be extracted reliably in this case. Thus, for the remainder of theoretical description, it will be assumed that the subject is nominally stationary at rest.

If the subject is at rest, the CP component can be extracted by first removing the mean over the data block, as described above, and then combining the I/Q components in such a way as to render the best estimate of chest-wall motion. As previously mentioned, the relatively small motion of the chest wall means that the CP arc can for all practical purposes be considered as a straight line. Therefore the I/Q components of the CP signal are essentially linearly related. Typically, the I/Q signals will be unequal in magnitude, depending on the orientation of this line in the complex plane (see FIG. 2B). For example, if the resultant phase is oriented mostly toward the right (real), the Q component of the CP signal will be larger than the I component; conversely, the I component will be larger than the Q signal if the resultant phase points mostly upward (imaginary).

In recent work, various means have been employed to extract the CP signal from the I/Q signals for further processing, including selection of the largest, and principal component analysis. Here, employ linear regression may be employed to establish the best mean-square fit of a straight line to the CP arc. This is roughly equivalent to the principal component approach, however, it is somewhat more straightforward to implement.

If the sampled I/Q signals after A/D conversion are denoted as i(n) and q(n),n=1, 2, ..., N, where N is the block length of the collected data, subtracting the mean value over the data block yields the zero-mean data:

$$\tilde{i}(n) = i(n) - \frac{1}{N}\sum_{n=1}^{N} i(n), \text{ and} \tag{1a}$$

$$\tilde{q}(n) = q(n) - \frac{1}{N}\sum_{n=1}^{N} q(n). \tag{1b}$$

Figure 3:
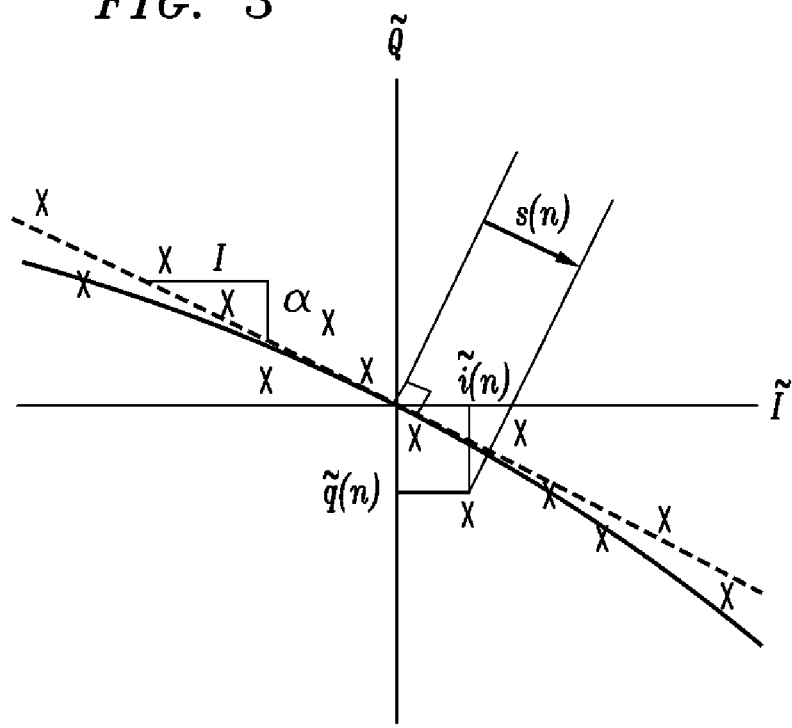
FIG. 3 is a geometrical diagram showing zero-mean I and Q data along the CP reflex arc.

A nominal linear relationship is assumed to exist between the I/Q components, so:

$$\tilde{q}(n) = a\tilde{i}(n) + v(n), \tag{2}$$

where a is the slope and v(n) represents additive noise or interference. FIG. 3 shows a diagram of what a typical data set (x's) might look like relative to the CP arc (solid) and its straight-line tangent (dashed). Linear regression determines the best estimate of the slope in the sense of minimizing the mean-square residual, and is given by:

$$\hat{a} = \frac{\sum_{n=1}^{N} \tilde{i}(n)\tilde{q}(n)}{\sum_{n=1}^{N} \tilde{i}^2(n)}. \tag{3}$$

With this slope estimate, the distance along the arc can be calculated as:

$$s(n) = \frac{\tilde{i}(n) + \hat{a}\tilde{q}(n)}{\sqrt{\hat{a}^2 + 1}}. \tag{4}$$

Thus, $s(n) = \tilde{i}(n)$ for the limiting case when $\hat{a}=0$, and likewise $s(n) = \tilde{q}(n)$ when $\hat{a}=\infty$. For intermediate values, $\hat{a}$ acts as a weighing factor to combine $\tilde{i}(n)$ and $\tilde{q}(n)$ optimally.

Note that although arc length is an appropriate measure of chest-wall motion, its scale is not inherently calibrated since the amplitude of the I/Q signals depends on transmitted power, chest-wall reflection coefficient, antenna and receiver gain and perhaps other factors. Therefore, if an absolute chest-wall displacement measurement is desired, it is necessary to calibrate the system under specified conditions. This can be most conveniently accomplished by having the subject rock back and fourth at a slow rate (e.g., period of 1-5 seconds) over at least a half wavelength (e.g., 6.25 am at 2.4 GHz), so that the I/Q signals trace out a full circle in the complex plane (c.f., FIG. 2B). Then, the voltage corresponding to the diameter of the circle thus traced out is known to correspond to an absolute arc length of $\lambda/2$ over $\pi$ (1.99 cm at 2.4 GHz). This calibration thus enables absolute measurements of chest-wall displacement due to respiration or heartbeat. An example of this will be given later in the experimental section.

C. Spectral Analysis

Conventional spectrum analysis is useful for estimating heart and respiration rates from the extracted CP signal. In this domain, the fundamental frequency along with associated harmonics appears as peaks in the spectrum, and the location of the fundamental determines an estimate of the rate. The well-known Welch weighted overlapped segment averaging (WOSA) method may be used, whereby a data record of N samples is subdivided into (possibly overlapping) M-sample sub-blocks, which are then weighted for sidelobe control, transformed using an M-point fast Fourier transform (FFT), magnitude-squared, and average. The higher the value of N/M, the more spectra are averaged, reducing the statistical variance of the power spectral density by a factor of approximately $\sqrt{N/M}$. From this standpoint, small values of the FFT size M are desirable. However, spectral resolution suffers as M is decreased, so a tradeoff exists between variance and resolution.

Alternatively, the extracted CP signal may be autocorrelated, windowed, and transformed by FFT (Blackman-Tukey method). In this case, windowing the autocorrelation reduces statistical variation of the spectrum at the expense of reduced spectral resolution, just like the tradeoff in WOSA spectrum analysis. The two techniques are roughly equivalent in this respect; no particular theoretical advantage of one over the other exists (see, e.g., Stoica, et al., *Introduction to Spectral Analysis*, Upper Saddle River, N.J.: Prentice Hall, 1997, ch. 2). However, the Welch method is usually preferred from implementation considerations.

Figure 4:
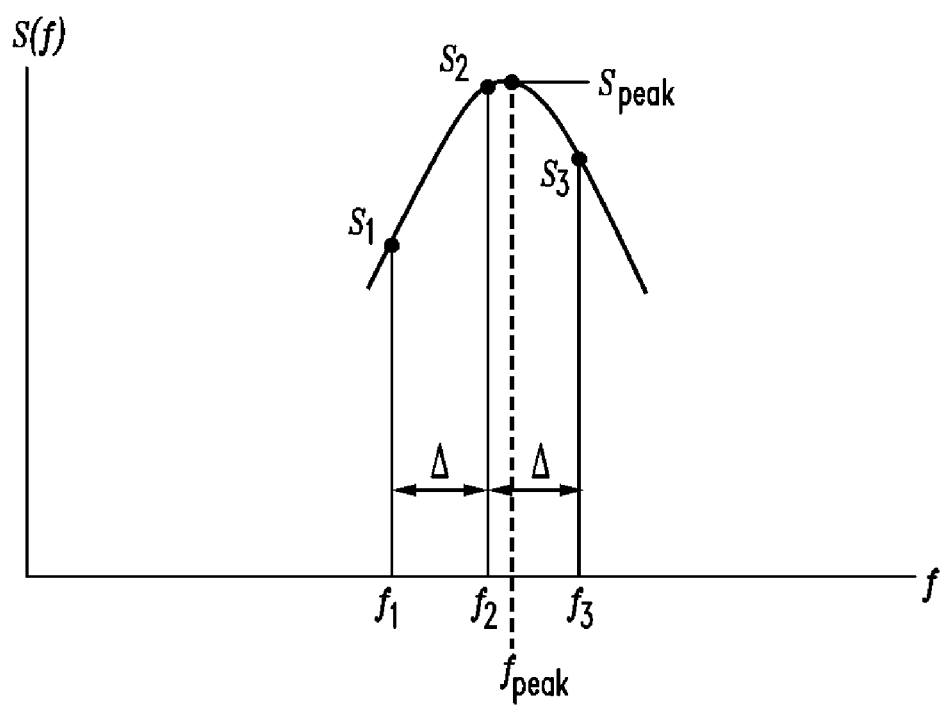
FIG. 4 is a geometrical diagram showing quadratic peak interpolation of the power spectrum.

With limited spectral resolution (necessitated by the desire to reduce spectral variation), the actual peak of the spectrum should be interpolated to achieve accurate heart and respiration rates. In one embodiment, a three-point quadratic interpolation is sufficient for this purpose. First the highest spectral value $S_2$ and corresponding frequency $f_2$ are identified within an appropriate range of the power spectrum. Then, values $f_1$ and $f_3$ are identified as the adjacent frequencies below and above $f_2$ respectively, along with their associated spectral values $S_1$ and $S_3$. A quadratic function is then fitted to the three points $S_1$, $S_2$, $S_3$, as depicted in FIG. 4, which yields the estimated peak frequency according to:

$$f_{peak} = \frac{\Delta}{2} \cdot \frac{S_3 - S_1}{2S_2 - S_1 - S_3} + f_2, \tag{5}$$

where it is assumed that $f_1$, $f_2$, $f_3$ are equally spaced by $\Delta$, i.e.:

$$\Delta = f_3 - f_2 = f_2 - f_1. \tag{6}$$

If the actual peak value is desired, that can also be easily determined, and is expressed as:

$$S_{peak} = S_2 + (S_3 - S_1) \frac{f_{peak} - f_2}{4\Delta} \tag{7}$$
$$= \frac{(4S_2 - S_1 - S_3)^2 - 4S_1 S_3}{8(2S_2 - S_1 - S_3)}.$$

IV. Enhancement of Heartbeat Signal

It will be demonstrated in the experiments below that periodic chest-wall motion due to respiration typically has many significant harmonics, which can interfere with reliable detection of the much smaller heartbeat signal. A technique will now be presented to enhance the weak heartbeat signal by subtracting out respiration harmonics.

The general signal processing problem in abstract terms is formulated as follows. $x(n) = s(n) + v(n)$ is a real signal composed of a desired signal component $s(n)$ and a periodic component $v(n)$ that is desired to be removed. The fundamental frequency of $v(n)$ is denoted as $f_0$, and an amplitude and a phase specify each of the harmonic components. If a single complex number $h_l$ is used to represent the amplitude and phase of the $l^{th}$ harmonic, the periodic disturbance can be expressed as:

$$v(n) = \Re\left(\sum_{l=1}^{L} h_l e^{jl\omega_0 n}\right), \tag{8}$$

where L is the number of significant harmonics, $\Re$ denotes the real part, and $\omega_0 = 2\pi f_0$. The effect of $v(n)$ over the data block of N samples should be minimized. Therefore, the cost function to be minimized is defined to be the mean-square error (MSE):

$$J = \frac{1}{N} \sum_{n=1}^{N} [x(n) - \hat{v}(n) - w_0]^2, \tag{9}$$

where $$\hat{v}(n) = \Re\left(\sum_{l=1}^{L} w_l e^{jl\hat{\omega}_0 n}\right) \tag{10}$$

is an estimate of $v(n)$, parameterized by the complex weights $w_l$, $l=1, \ldots, L$ and the estimated fundamental (angular) frequency $\hat{\omega}_0$, and where a (complex) DC term $w_0$ is included for completeness. The DC value that minimizes J is given by:

$$w_{0,min} = \frac{1}{N} \sum_{n=1}^{N} [x(n) - \hat{v}(n)]. \tag{11}$$

Therefore, J can be replaced with the modified cost function:

$$\tilde{J} = \frac{1}{N} \sum_{n=1}^{N} \left[\tilde{x}(n) - \Re\left(\sum_{l=1}^{L} w_l \tilde{e}_l(n)\right)\right]^2, \tag{12}$$

where:

$$\tilde{x}(n) = x(n) - \frac{1}{N} \sum_{m=1}^{N} x(m), \text{ and} \tag{13}$$

$$\tilde{e}_l(n) = e^{jl\hat{\omega}_0 n} - \frac{1}{N} \sum_{m=1}^{N} e^{jl\hat{\omega}_0 m} \tag{14}$$

are of zero-mean over the data block, so that now only the L coefficients $\omega_l$, $L=1, \ldots, L$ need to be minimized.

Figure 5:
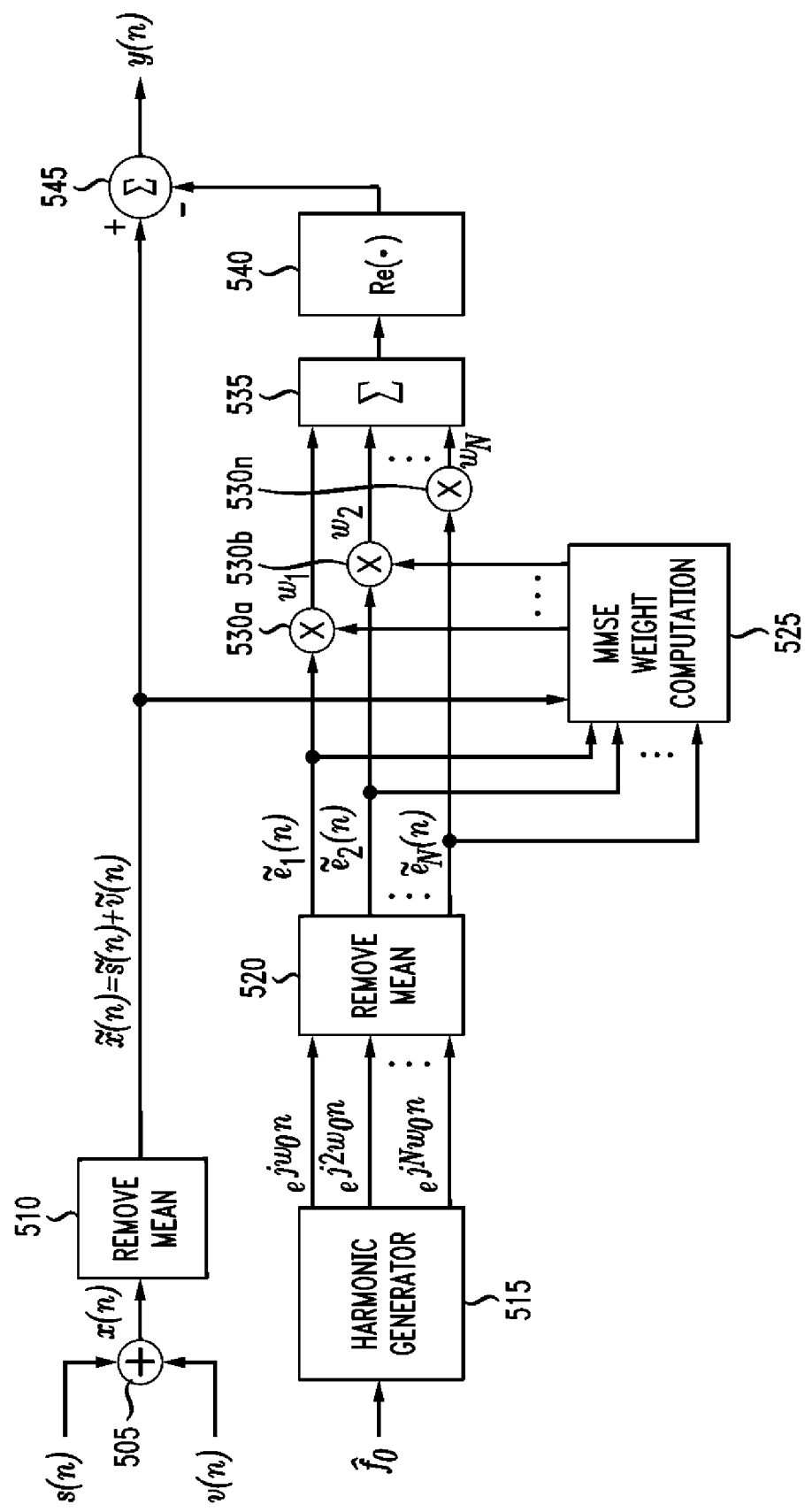
FIG. 5 is a block diagram of one embodiment of a harmonic canceller.

FIG. 5 is a block diagram of an embodiment of a harmonic canceller. s(n) and v(n) are summed in a summing junction 505 and the mean removed in a remove mean block 510. $f_0$ is received into a harmonic generator 515, which produces harmonics thereof. The means of the harmonics are removed in a remove mean block 520. The output of the remove mean blocks 510, 520 are provided to a minimum MSE weight computation block 525, which produces weights based thereon. These weights are then applied to the outputs of the remove mean block 520 in various multiplication junctions 530a, 530b, 530n. The resulting weighted outputs are then summed in a summer 535. A resultant is computed in a block 540. That resultant is applied to the output of the remove mean block 510 in a summing junction 545 to yield the output y(n).

A mathematical expression for the weights that minimize $\tilde{J}$ can now be derived. First, a cross correlation vector r is defined having components:

$$r_l = \frac{1}{N}\sum_{n=1}^{N} \tilde{x}(n)\tilde{e}_l^*(n), \tag{15}$$

and the Hermitian and (symmetric) complementary correlation matrices R and C are defined having components:

$$R_{lm} = \frac{1}{N}\sum_{n=1}^{N} \tilde{e}_l(n)\tilde{e}_m^*(n), \text{ and} \tag{16}$$

$$C_{lm} = \frac{1}{N}\sum_{n=1}^{N} \tilde{e}_l^*(n)\tilde{e}_m^*(n). \tag{17}$$

Using these definitions, the cost function of Equation (12) can be rewritten as:

$$\tilde{J} = P_{\tilde{x}} + 2\Re(r^H w) + \frac{1}{2}w^H Rw + \frac{1}{2}\Re(w^T C^* w) \tag{18}$$

where:

$$P_{\tilde{x}} = \frac{1}{N}\sum_{n=1}^{N} \tilde{x}^2(n) \tag{19}$$

is the input power, $w=[w_1\ w_2\ \ldots\ w_L]^T$, and the superscripts T and H denote, respectively, the transpose and the (Hermitian) complex conjugate transpose.

The cost function $\tilde{J}$ is minimized by differentiating Equation (18) with respect to w* and equating to zero, giving:

$$\frac{d\tilde{J}}{dw^*} = -r + \frac{1}{2}Rw + \frac{1}{2}Cw^* = 0. \tag{20}$$

In minimizing such quadratic forms, w and w* can be considered as independent variables; see, e.g., Brandwood, "A Complex Gradient Operator and Its Application in Adaptive Array Theory," IEEE Proc, Pts. F and H, vol. 130, pp. 11-16, February 1983). Premultiplying the conjugate of Equation (20) by $CR^{-*}$ gives:

$$CR^{-*}\left(\frac{d\tilde{J}}{dw^*}\right)^* = -CR^{-*}r^* + \frac{1}{2}Cw^* + \frac{1}{2}CR^{-*}C^*w = 0. \tag{21}$$

Subtracting Equation (21) from Equation (20) and solving for w then gives the optimal weight:

$$w_{min} = 2(R - CR^{-*}C^*)^{-1}(r - CR^{-*}r^*). \tag{22}$$

The Orthogonality Principle dictates that the error inside the brackets of Equation (12) is orthogonal to each $\tilde{e}_l(n)$ and $\tilde{e}_l^*(n)$, l=1, 2, ..., L, hence, the minimum cost function is:

$$\tilde{J}_{min} = \frac{1}{N}\sum_{n=1}^{N}\left[\tilde{x}(n) - \Re\left(\sum_{l=1}^{L}\omega_{l,min}\tilde{e}_l(n)\right)\right]\tilde{x}(n) = P_{\tilde{x}} - \Re(r^H w_{min}). \tag{23}$$

As the block size N becomes very large, R→I, the identity matrix, and C→0, the latter because the average value of a sinusoid tends to zero over a long interval. Also, in this case, Equations (15) and (8) show that $$r \to \frac{h}{2},$$

where $h=[h_1\ h_2\ \ldots\ h_L]^T$, assuming that s(n) has no harmonic components in common with those of the disturbance v(n). Hence, from Equation (22), $w_{min}$→h, which is the desired solution. Thus, when N is very large, C can be neglected. However, for short, and even moderate-size, data blocks, C is not negligible and must be included to achieve accurate harmonic cancellation.

What remains is estimating the fundamental frequency $f_0$. For the heartbeat enhancement application, the fundamental frequency of the respiration should be estimated. The fundamental frequency of the respiration may be estimated in the same way that the heart rate was estimated above, i.e., spectrum analysis with three-point quadratic interpolation. However, in some cases three-point quadratic interpolation may not be accurate enough, since respiration occurs at a lower frequency, and also because more accuracy is required for the higher harmonic frequencies to achieve good cancellation. In this case, a second step may be taken to refine the estimate, whereby the residual signal power variation is observed as the initial estimate is slightly perturbed.

Consider a single discrete-time sinusoid cos ωn of an (imprecisely known) normalized frequency $$f = \frac{\omega}{2\pi},$$

and suppose that this tone may be canceled by subtracting another scaled and phase-shifted sinusoid of normalized frequency $$\hat{f} = \frac{\hat{\omega}}{2\pi}$$

(which is an estimate of f). This may be handled as a special case of Equations (12) through (14) for L=1, in which case the MSE cost function is:

$$\tilde{J}_1 = \frac{1}{N}\sum_{n=0}^{N-1}\{\tilde{x}(n) - \Re[w\tilde{e}(n)]\}^2, \tag{24}$$

where:

$$\tilde{x}(n) = \cos\omega n - \frac{1}{N}\sum_{m=0}^{N-1}\cos\omega m = \cos\omega n - \frac{1}{N}\Re\left(\frac{1-e^{j\omega N}}{1-e^{j\omega}}\right), \tag{25}$$

w is a single complex weight, $$\tilde{e}(n) \equiv e^{j\tilde{\omega}n} - \frac{1}{N}\sum_{m=0}^{N-1} e^{j\tilde{\omega}m} = e^{j\tilde{\omega}n} - \frac{1}{N} \cdot \frac{1-e^{j\tilde{\omega}N}}{1-e^{j\tilde{\omega}}} \quad (26)$$

and where, for mathematical convenience in this analysis, the N-sample data block is indexed from 0 to N−1. Similarly, as special cases of Equations (23), (19), (22), (15), (16) and (17):

$$\tilde{J}_{1,min} = P_{\tilde{x}} - \Re(r^* w_{min}). \quad (27)$$

where:

$$P_{\tilde{x}} = \frac{1}{N}\sum_{n=0}^{N-1} \tilde{x}^2(n) = \frac{1}{N}\sum_{n=0}^{N-1}\left[\cos\omega n - \frac{1}{N}\Re\left(\frac{1-e^{j\omega N}}{1-e^{j\omega}}\right)\right]\cos\omega n = \frac{1}{2}\left[1 + \frac{1}{N}\Re\left(\frac{1-e^{j2\omega N}}{1-e^{j2\omega}}\right)\right] - \frac{1}{N^2}\left[\Re\left(\frac{1-e^{j\omega N}}{1-e^{j\omega}}\right)\right]^2 \quad (28)$$

in which the zero-mean property of $\tilde{x}(n)$ and the identity $$\cos^2\omega n = \frac{1+\cos 2\omega n}{2}$$

have been employed, and:

$$w_{min} = \frac{2}{R - \frac{|C|^2}{R}}\left(r - \frac{C}{R}r^*\right), \quad (29)$$

with $$r = \frac{1}{N}\sum_{n=0}^{N-1} \tilde{x}(n)\tilde{e}^*(n) = \frac{1}{N}\sum_{n=0}^{N-1}\left[\cos\omega n - \frac{1}{N}\Re\left(\frac{1-e^{j\omega N}}{1-e^{j\omega}}\right)\right]e^{-j\tilde{\omega}n} = \frac{1}{2N}\left[\frac{1-e^{-j(\tilde{\omega}+\omega)N}}{1-e^{-j(\tilde{\omega}+\omega)}} + \frac{1-e^{-j(\tilde{\omega}-\omega)N}}{1-e^{-j(\tilde{\omega}-\omega)}}\right] - \frac{1}{N^2}\Re\left(\frac{1-e^{j\omega N}}{1-e^{j\omega}}\right)\frac{1-e^{-j\tilde{\omega}N}}{1-e^{-j\tilde{\omega}}} \quad (30)$$

in which the zero-mean property of $\tilde{x}(n)$ has again been employed and the exponential of $\cos \omega n$, $$R = \frac{1}{N}\sum_{n=0}^{N-1}|\tilde{e}(n)|^2 = 1 - \frac{1}{N^2}\left|\frac{1-e^{j\tilde{\omega}N}}{1-e^{j\tilde{\omega}}}\right|^2 \quad (31)$$

in which the zero-mean property of $\tilde{e}(n)$ has been employed, and $$C = \frac{1}{N}\sum_{n=0}^{N-1}[\tilde{e}^*(n)]^2 = \frac{1}{N}\cdot\frac{1-e^{-j2\tilde{\omega}N}}{1-e^{-j2\tilde{\omega}}} - \frac{1}{N^2}\left(\frac{1-e^{-j\tilde{\omega}N}}{1-e^{-j\tilde{\omega}}}\right)^2. \quad (32)$$

For large N, R→1, C→0, and $w_{min}$→2r, where, from Equation (30):

$$r \to \frac{1}{2N}\left[\frac{1-e^{-j(\tilde{\omega}+\omega)N}}{1-e^{-j(\tilde{\omega}+\omega)}} + \frac{1-e^{-j(\tilde{\omega}-\omega)N}}{1-e^{-j(\tilde{\omega}-\omega)}}\right], \quad (33)$$

and from Equation (28), $$P_{\tilde{x}} \to \frac{1}{2}.$$

In addition, when |f̃−f| is small, the first term of Equation (33) can be neglected. Therefore, from Equation (27), the normalized MSE is approximated as:

$$\frac{\tilde{J}_{1,min}}{P_{\tilde{x}}} \approx 1 - \left|\frac{\sin\frac{(\tilde{\omega}-\omega)N}{2}}{\frac{(\tilde{\omega}-\omega)N}{2}}\right|^2, \quad N \gg 1 \text{ and } |\tilde{f}-f|N \ll 1 \quad (34)$$

$$\overrightarrow{\tilde{\omega}\to\omega} \frac{N^2-1}{12}(\tilde{\omega}-\omega)^2. \quad (35)$$

Thus, when the frequency estimate is close to its optimal value, the selectivity of the harmonic canceller MSE varies as the square of the frequency error. This means that three-point quadratic interpolation can be applied with substantial accuracy to refine the initial estimate $\tilde{\omega}$. Accordingly, $\tilde{\omega}$ is perturbed slightly as $\tilde{\omega}\pm\Delta$ to yield three measurements of the MSE, which are then interpolated to yield the refined estimate. If $J_1, J_2, J_3$ denote the MSE at frequencies $\tilde{\omega}-\Delta, \tilde{\omega}, \tilde{\omega}+\Delta$, respectively, fitting a quadratic to this data to find the minimum yields the refined estimate:

$$\hat{\omega} = \frac{\Delta}{2}\cdot\frac{J_3 - J_1}{2J_2 - J_1 - J_3} + \tilde{\omega}. \quad (36)$$

Figure 6:
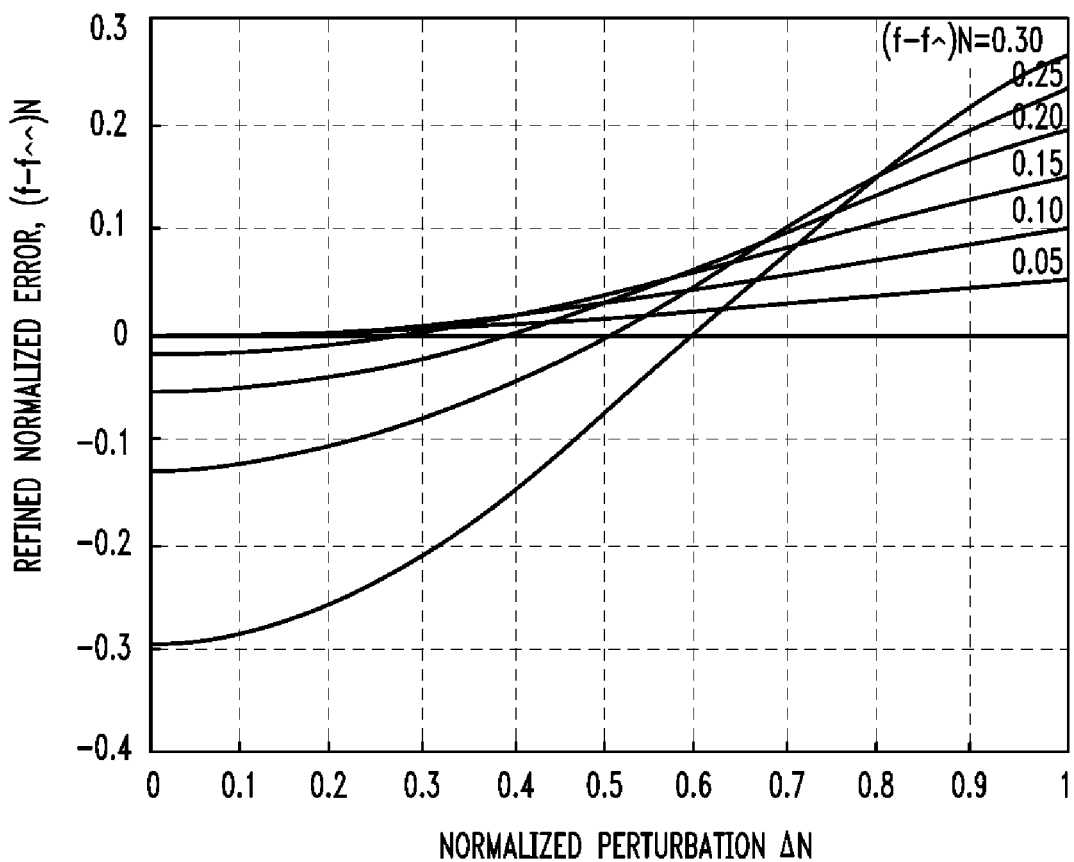
FIG. 6 is a plot showing the effect of normalized perturbation on the refined normalized error for different values of initial normalized error.

In the above process, the question naturally arises as to just how large the perturbation $\Delta$ may be to obtain the best accuracy of the refined estimate. If $\Delta$ is too small, the minimum for accurate interpolation may not be approached. On the other hand, if $\Delta$ is too large, the MSE may no longer be well-characterized as quadratic. To give some idea on the choice of $\Delta$, N is assumed to be large enough, and |f̃−f|N is assumed to be small enough so that Equation (34) is a good approximation to the MSE. FIG. 6, which was calculated from Equation (36) using the simplified model of Equation (34), shows how the refined normalized error (f−f̂)N depends on the initial normalized error (f−f̃)N and the normalized perturbation $\Delta$N. Naturally, as f̃ becomes close to f, f̂ also becomes close to f over a very large range of $\Delta$. However, as f̃ becomes further away from f, the range of "good" values of $\Delta$ becomes smaller.

As an example, suppose that the actual frequency of the tone to be cancelled is 0.25 Hz over T=20 s with a 50 Hz sampling rate, so that the normalized frequency is $$\frac{0.25}{50} = 0.005$$

and N=50·20=1000 is the number of samples. For a 2% error in the initial estimate, $(f-\hat{f})N=0.02 \cdot 0.005 \cdot 1000=0.1$, which is small enough to allow Equation (34) to apply. FIG. 6 shows that $\Delta N \approx 0.3$ is optimal. This means that an optimal normalized frequency perturbation lies at $\pm \Delta = \pm 0.0003$, or $\pm 6\%$, for realizing the best refined estimate.

The analysis may now be extended to the case where the tone to be cancelled is slowly varying in a random way, thus forming a nonstationary process. Suppose that the frequency variation is Gaussian with probability density:

$$f(\omega) = \frac{1}{\sqrt{2\pi}\,\sigma} \exp\left[-\frac{(\omega - \overline{\omega})^2}{2\sigma^2}\right], \tag{37}$$

where $\overline{\omega}$ is the mean frequency and $\sigma$ is the standard deviation. Using the approximation of Equation (35) with Equation (37), the expected value of the MSE is calculated as:

$$E\tilde{J}_{1,min} \approx \frac{N^2-1}{12} \int (\omega - \hat{\omega})^2 f(\omega) d\omega = \frac{N^2-1}{12}[\sigma^2 + (\overline{\omega} - \hat{\omega})^2]. \tag{38}$$

Therefore, the expected MSE is still quadratic as it was in Equation (35), the only difference being a shift due to the additional term $\sigma^2$. Note that Equation (38) is consistent with Equation (35) as $\sigma \to 0$.

If $\omega$ remains substantially constant over the interval T, Equation (38) can be interpreted in an ensemble sense, i.e., the result one that would be obtained were many realizations averaged. On the other hand, if $\omega$ varies considerably over T, yet not too fast, Equation (38) reasonably describes the MSE over a single realization.

Finally, the case where a harmonic complex with a fundamental frequency $\omega$ should be canceled is considered, viz.:

$$\sum_{l=1}^{L} \sqrt{2P_l} \cos(l\omega n + \phi_l), \tag{39}$$

where $P_l$ and $\phi_l$, $l=1, 2, \ldots, L$, are, respectively, arbitrary powers and phases of the fundamental and its L−1 harmonics. If N is large enough to encompass many cycles of the fundamental, all of the harmonics will be virtually uncorrelated over the interval and the total minimum MSE can be approximated as the sum of the individual MSEs, giving:

$$\tilde{J}_{L,min} \approx \frac{N^2-1}{12} \sum_{l=1}^{L} P_l(l\omega - l\hat{\omega})^2 = \frac{N^2-1}{12}(\omega - \hat{\omega})^2 \sum_{l=1}^{L} l^2 P_l. \tag{40}$$

Thus, for cancellation of multiple harmonics, the MSE will still be proportional to the square of the difference between the fundamental frequency and its initial estimate. And, of course, for L=1 and $P_1=1$, Equation (40) reduces to Equation (35) as it should.

To summarize the above, when the frequency estimate is close to the true value, the selectivity of the canceller output MSE varies as the square of the frequency error. Therefore, the three-point quadratic interpolation process can be applied with great accuracy to the total MSE in order to refine the estimate of the fundamental respiration frequency.

V. Simulation

A test signal that represents chest-wall motion due to both heartbeat and respiration will now be developed and employed to demonstrate the above-described signal processing techniques. Section VI will then validate and extend the simulation results using experimental data collected with a real RF Doppler radar system using a live, human subject.

A. Test Signal

The test signal represents chest-wall motion at discrete times $$t = \frac{n}{f_s}, n = 1, 2, \ldots, N,$$

where $f_s$ is the sampling frequency, and is denoted:

$$x(n) = x_H(n) + x_R(n), \tag{41}$$

where $x_H(n)$ and $x_R(n)$ are, respectively, the heartbeat and respiration signal components.

For the heartbeat signal component, a characteristic analog pulse shape $p_H(t)$ that periodically repeats every $$\frac{1}{f_H}$$

s is assumed, where $f_H$ is the heartbeat frequency in Hz (heart rate of $60 f_H$ in bpm). The analog pulse shape described herein is an exponential $$e^{-\frac{t}{\tau}},$$

with time constant $\tau$, filtered by a second-order Butterworth (critically-damped) filter with cutoff frequency $f_0$. Motivating this model is the realization that the emptying of the heart ventricles that occurs during the systolic phase likely imparts a short impulsive motion that is subsequently filtered by the bone and tissue before being sensed on the chest wall.

The Laplace transforms of the exponential and Butterworth filter impulse response are expressed as, respectively:

$$L\{e^{-\frac{t}{\tau}}\} = \frac{1}{\frac{s+1}{\tau}}. \tag{42}$$

and

-continued $$L\left\{\frac{\sqrt{2}}{\omega_0}e^{-\frac{\omega_0 t}{\sqrt{2}}}\sin\frac{\omega_0 t}{\sqrt{2}}\right\} = \frac{1}{s^2+\sqrt{2}\,\omega_0 s+\omega_0^2}, \quad (43)$$

where $\omega_0=2\pi f_0$. Thus, the Laplace transform of the pulse shape is taken as the product of Equations (42) and (43), which can be expressed using a partial fraction expansion as:

$$\frac{1}{s+\frac{1}{\tau}} \cdot \frac{1}{s^2+\sqrt{2}\,\omega_0 s+\omega_0^2} = \frac{1}{C}\left(\frac{1}{s+\frac{1}{\tau}} + \frac{-s+\frac{1}{\tau}-\sqrt{2}\,\omega_0}{s^2+\sqrt{2}\,\omega_0 s+\omega_0^2}\right), \quad (44)$$

where:

$$C = \frac{1}{\tau^2} + \frac{\sqrt{2}\,\omega_0}{\tau} + \omega_0^2 \quad (45)$$

is an unimportant constant that will be subsequently neglected. The inverse Laplace transform of the first term in parentheses above can be immediately identified from Equation (42), while the inverse Laplace transform of the second term can be determined from Equation (43) and by differentiating the impulse response on the left side of Equation (43), yielding:

$$L\left\{e^{-\frac{\omega_0 t}{\sqrt{2}}}\left(\cos\frac{\omega_0 t}{\sqrt{2}} - \sin\frac{\omega_0 t}{\sqrt{2}}\right)\right\} = \frac{s}{s^2+\sqrt{2}\,\omega_0 s+\omega_0^2}, \quad (46)$$

With some algebra, the normalized pulse shape is determined as:

$$p_H(t) = L^{-1}\left\{\frac{1}{s+\frac{1}{\tau}} + \frac{-s+\frac{1}{\tau}-\sqrt{2}\,\omega_0}{s^2+\sqrt{2}\,\omega_0 s+\omega_0^2}\right\} = \quad (47)$$

$$e^{-\frac{t}{\tau}} + \left[\left(\frac{\sqrt{2}}{\omega_0\tau}-1\right)\sin\frac{\omega_0 t}{\sqrt{2}} - \cos\frac{\omega_0 t}{\sqrt{2}}\right]e^{-\frac{\omega_0 t}{\sqrt{2}}}.$$

Finally, $p_H$ periodically repeats at intervals of $$\frac{1}{f_H}$$

and sampled at $f_s$ to obtain the discrete-time heartbeat signal component:

$$x_H(n) = p_H\left(\frac{n}{f_s} - \left\lfloor\frac{n}{f_s}f_H\right\rfloor \cdot \frac{1}{f_H}\right), \quad (48)$$

where $\lfloor x \rfloor$ (the "floor") is defined as the greatest integer less than or equal to x. Thus, samples $$p_H\left(\frac{n}{f_s}\right)$$

are sequentially taken until $$\frac{n}{f_s}$$

reaches the heart-rate period $$\frac{1}{f_H},$$

at which point the next pulse is started, and so on. The resulting signal component is then scaled to the peak-to-peak value $A_H$.

In a similar way, a prototype respiration pulse may be defined as:

$$p_R(t) = \sin^p \pi f_R t, \; 0 \le t \le \frac{1}{f_R}, \quad (49)$$

which is a half-cycle of a sinusoid raised to the $p^{th}$ power. The motivation for this comes from the examination of real data, where the respiratory chest-wall motion is similar to a sinusoidal half-cycle with a rounded cusp. The exponent p controls the rounding of the cusp as well as the general shape. $p_R(t)$ is regularly repeated at intervals of $$\frac{1}{f_R}$$

and sampled to obtain the discrete-time respiration signal component:

$$x_R(n) = p_R\left(\frac{n}{f_s} - \left\lfloor\frac{n}{f_s}f_R\right\rfloor \cdot \frac{1}{f_R}\right), \quad (50)$$

which is then scaled to peak-to-peak value $A_R$.

Figure 7A:
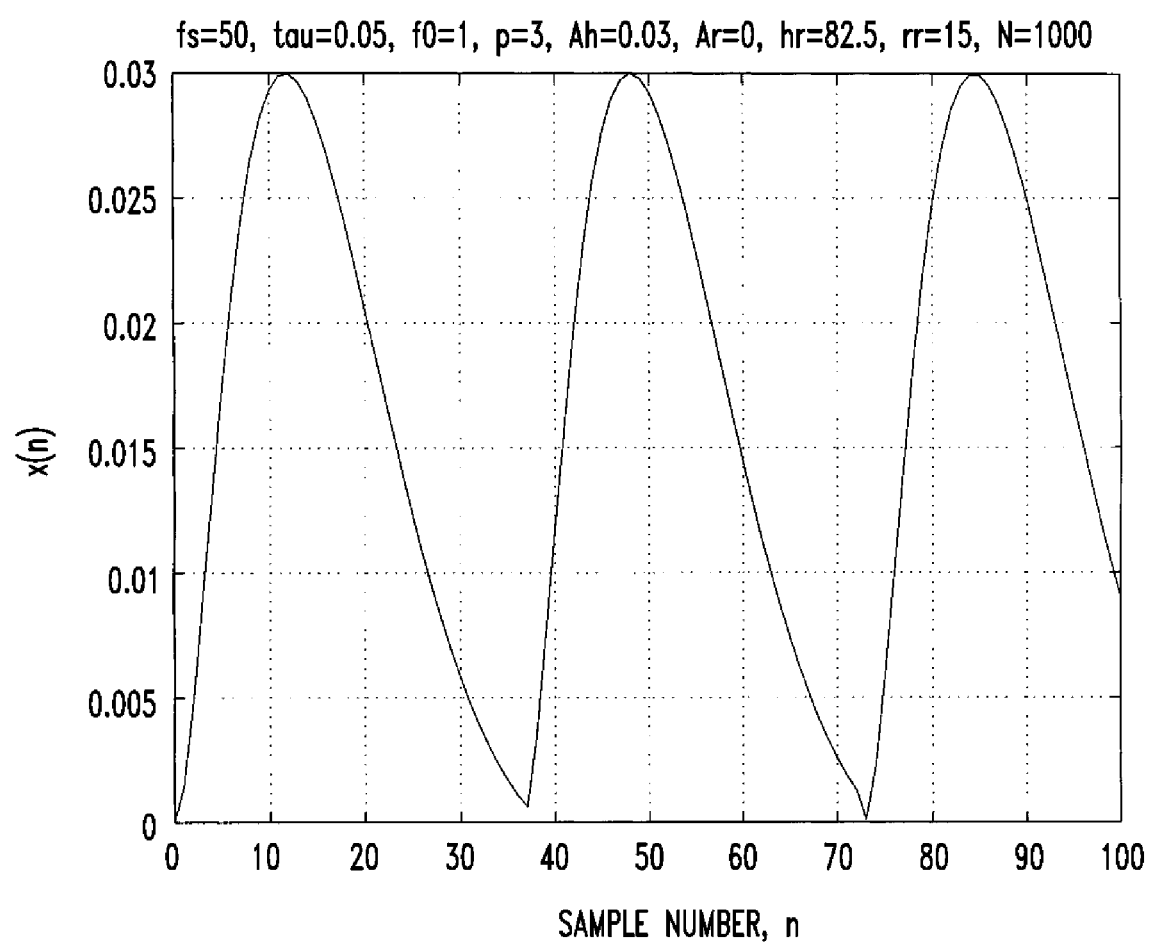
FIG. 7A is a plot of 100 samples of a heartbeat component of a test signal at a sampling rate $f_s=50$ Hz over $N=1000$ samples, with pulse parameters $\tau=0.05$ s and $f_0=1$ Hz, a peak-to-peak amplitude $A_H=0.03$ and a heart rate of 82.5 bpm ($f_H=1.375$ Hz)
Figure 7B:
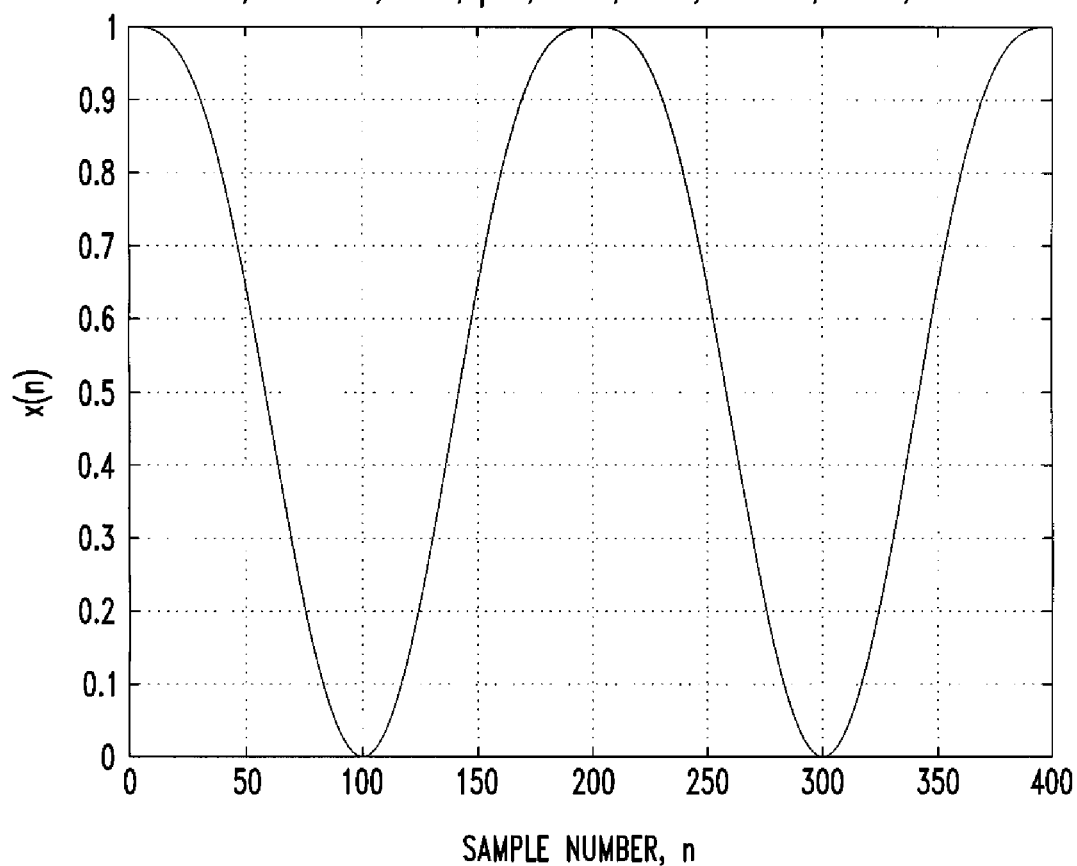
FIG. 7B is a plot of 400 samples of a respiration component of the test signal of FIG. 7A, with a characteristic exponent $p=3$, a peak-to-peak amplitude $A_R=1$ and a respiration rate of 15 bpm ($f_R=0.25$ Hz)
Figure 7C:
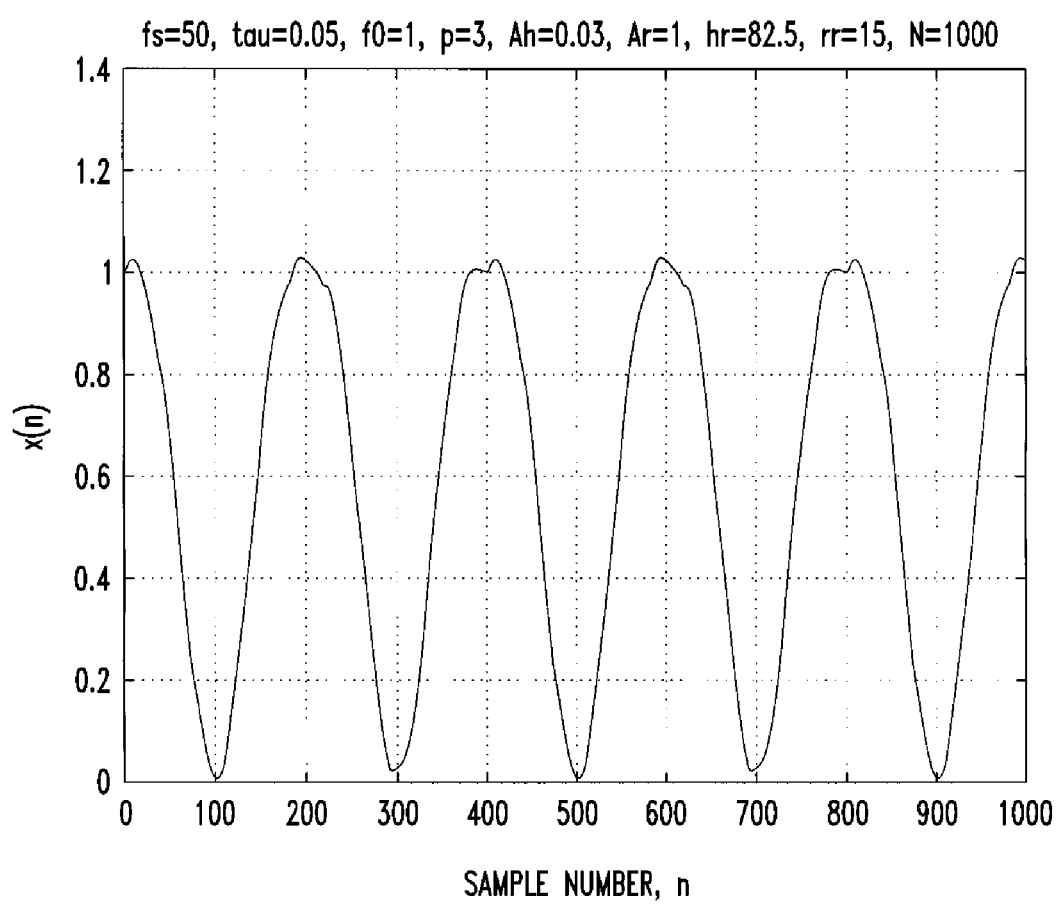
FIG. 7C is a plot of all 1000 samples of the combined heartbeat and respiration components of the test signal of FIG. 7A.

FIGS. 7A-C show the components of the test signal for parameter values that simulate a typical real signal from a live subject. A total of N=1000 samples (20 s) are generated at a sampling rate $f_s$=50 Hz. The heartbeat component is of peak-to-peak amplitude $A_H$=0.03 (3%) relative to the respiration peak-to-peak amplitude $A_R$=1. The heart rate is 82.5 bpm ($f_H$=1.375 Hz), and the respiration rate is 15 bpm ($f_R$=0.25 Hz). The other waveform parameters were selected to best match typical data. FIG. 7A shows the heartbeat component (100 samples displayed) with pulse parameters $\tau$=0.05 s and $f_0$=1 Hz, where the repeated Butterworth-like pulse shapes are readily apparent. FIG. 7B shows the respiration component (400 samples displayed) for p=3 and exhibits the prototypical half cycle pulse with rounded cusps. Finally, FIG. 7C shows the combined signal (all 1000 samples).

B. Spectral Analysis

Figure 8:
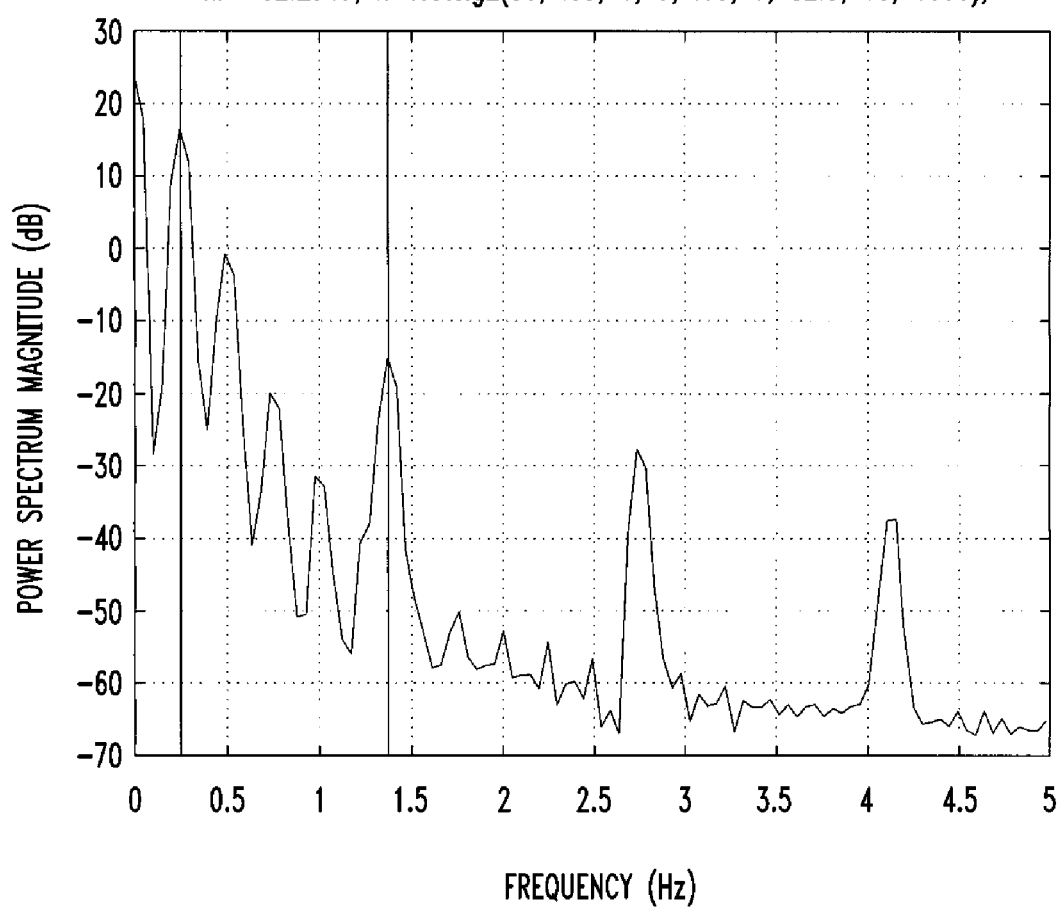
FIG. 8 is a plot of the power spectrum of the test signal of FIG. 7C.

FIG. 8 shows the power spectrum of the simulated test signal of FIG. 7C. The respiration fundamental is apparent at 0.25 Hz (15 bpm), and the heartbeat signal is apparent at 1.375 Hz (82.5 bpm), with relative amplitudes about 30 dB apart. Also seen are at least ten harmonics of the respiration and the second and third harmonics of the heartbeat.

In the illustrated embodiment, the estimated respiration frequency is calculated by first finding the largest spectral value in the frequency range of 0.1-1 Hz (6-60 bpm) and then using the three-point peak interpolation of Equation (5). The result of this calculation is an estimated respiration rate of 14.8296 bpm (0.2472 Hz), which is plotted in FIG. 8 as a solid vertical line. This estimate is within about 1% of the actual respiration rate of 15 bpm (0.25 Hz).

The estimated heartbeat frequency can be calculated in a similar manner, in this case by first finding the largest spectral value in the frequency range of 0.75-5 Hz (45-300 bpm) and again using Equation (5), giving an estimated heart rate of 82.2949 bpm (1.3716 Hz), which is plotted in FIG. 8 as a solid vertical line. This estimate is within 0.25% of the actual heart rate of 82.5 bpm (1.375 Hz), being even more accurate than the respiration rate estimate because the higher frequency is more resolvable for a fixed FFT size.

In general, the success of heart-rate estimation depends on the particular rates and amplitudes of the heartbeat and respiration components, as well as the frequency range over which one searches. In some cases, respiration harmonics can easily exceed the heartbeat component, thereby giving rise to false heart-rate estimates. In addition, for the example of FIG. 8, the heartbeat spectral peak just happens to fall between two respiration harmonics. If one of the respiration harmonics is close to the heart rate, signal cancellation may actually occur, which is even more problematic. One remedy to this problem will now be described.

C. Harmonic Cancellation

Figures 9A, 9B, 9C:
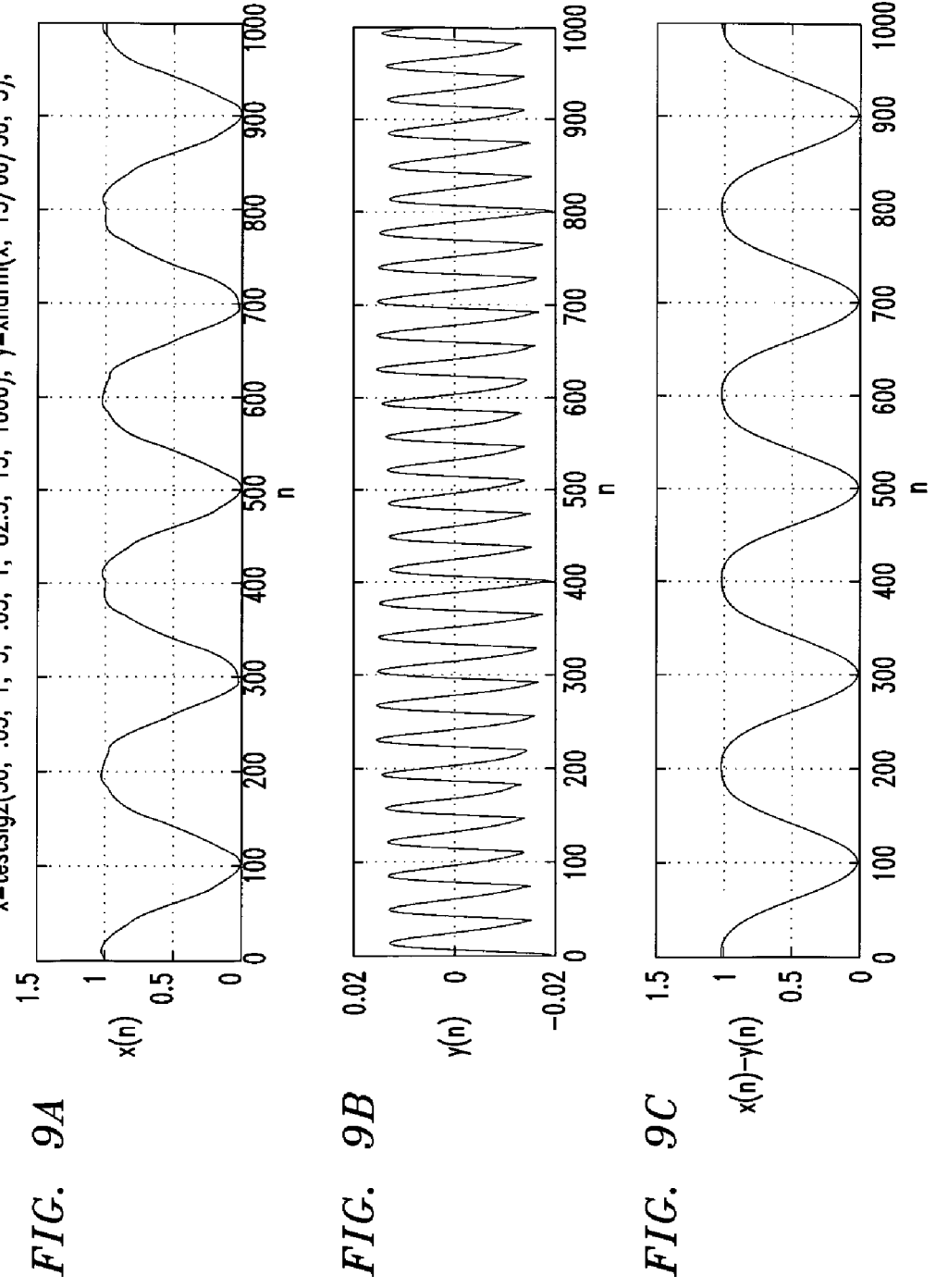
FIGS. 9A-C are plots representing cancellation of the first $L=5$ respiration harmonics of the test signal of FIG. 7C, showing the test signal input (FIG. 9A), an enhanced heartbeat output (FIG. 9B) and an enhanced respiration signal (FIG. 9C) obtained by subtracting the output from the input.

Here, the harmonic cancellation technique of Section IV is demonstrated. FIGS. 9A-C show the result of canceling the first L=5 respiration harmonics of the test signal of FIG. 7C, showing the input (FIG. 9A), enhanced heartbeat output (FIG. 9B), and also the enhanced respiration signal (FIG. 9C) obtained by subtracting the output from the input.

Figure 10:
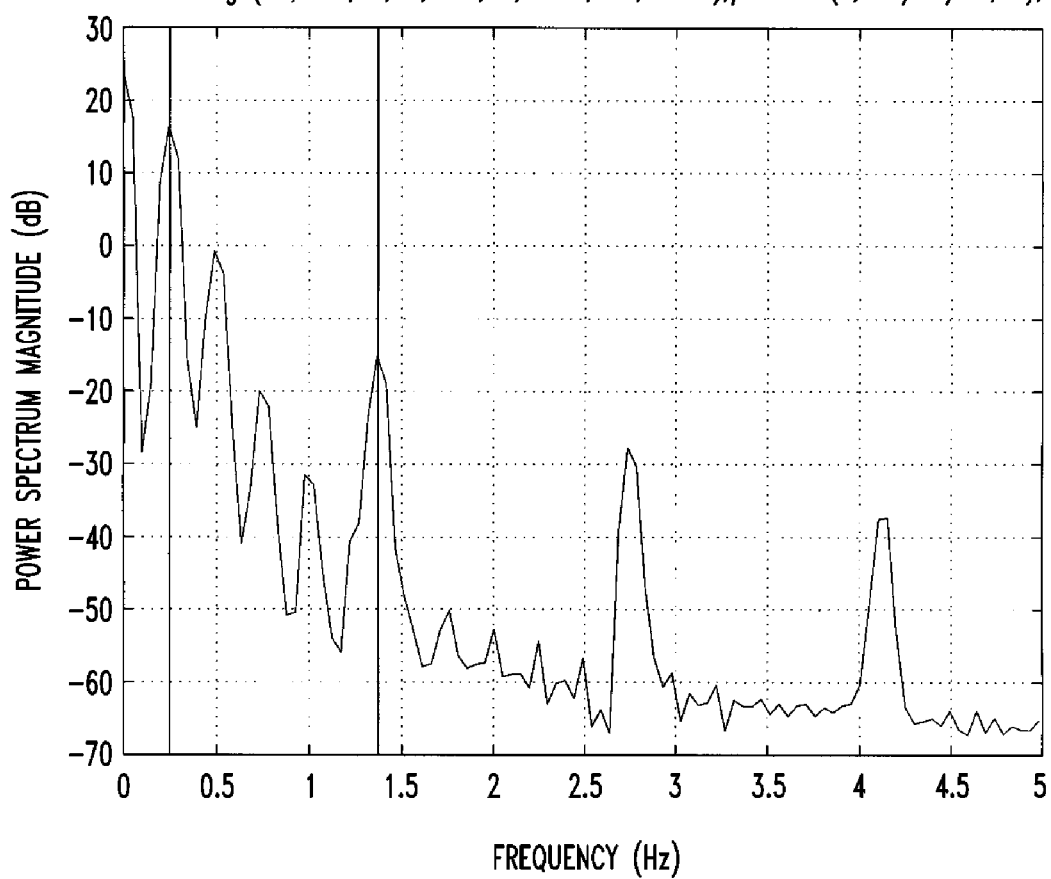
FIG. 10 is a plot of the power spectrum of the test signal of FIG. 7C after the respiration harmonic cancellation of FIG. 9B.

FIG. 10 shows the power spectrum of the enhanced heartbeat signal. Comparing this with FIG. 8 shows that the first five respiration harmonics have been substantially reduced, enabling much more reliable estimation of the heart rate. Some judgment may be needed in selecting the number of harmonics, L, to be cancelled. Certainly, L should be large enough to reduce the significant respiration harmonics below the heart rate to eliminate this interference. But if L is too large, what starts out as small respiration harmonics above the heart rate will actually increase somewhat because of leakage from the heartbeat spectral component. The value L=5 was selected here after some trial and error, but the choice is not critical.

In the above harmonic cancellation, the respiration rate is known exactly because it is specified for the test signal. As a result, the cancellation of the respiration harmonics is perfect. However, in a real setting, the respiration rate should first be estimated and then employed instead. As described above, and making a transposition from relative frequency to actual frequency, the relative MSE is given by:

$$\frac{\left[\pi(f_R - \hat{f}_R)T\right]^2}{3}, \quad (51)$$

where T is the processing interval and $f_R$ and $\hat{f}_R$ are, respectively, the actual and estimated respiration frequencies. Therefore, in the above example for $f_R$=0.25 Hz and T=20 s, one would expect that for a 1% respiration rate error, the relative residual harmonic level would be about $$\frac{(\pi \cdot 0.01 \cdot 0.25 \cdot 20)^2}{3} = 0.0082$$

(−20.8 dB), and would increase by 6 dB for every frequency error doubling above 1%.

Figure 11A:
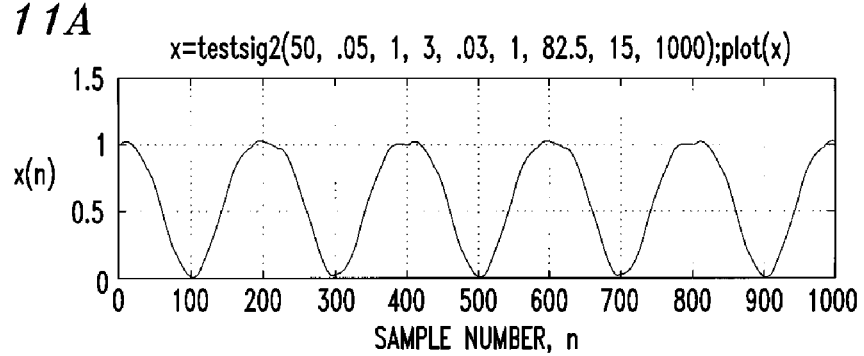
FIGS. 11A-D are plots reflecting a sensitivity of harmonic cancellation to the fundamental frequency estimate, showing from top to bottom, the input test signal of FIG. 6C (FIG. 11A) and output signals with −1% error (FIG. 11B), 0% error (FIG. 11C) and +1% error (FIG. 11A)
Figure 11B:
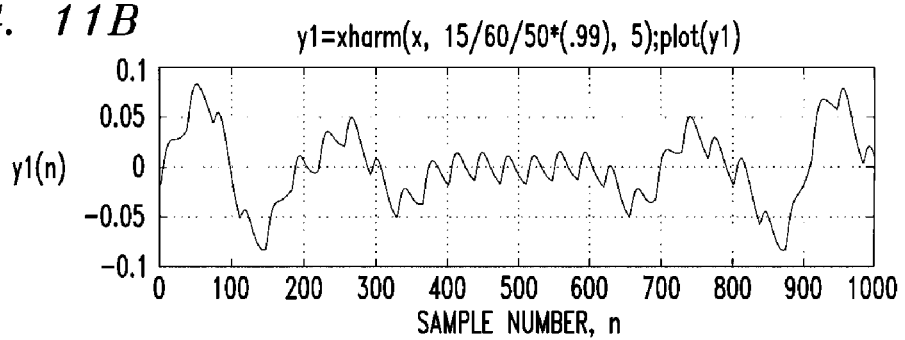
Figure 11C:
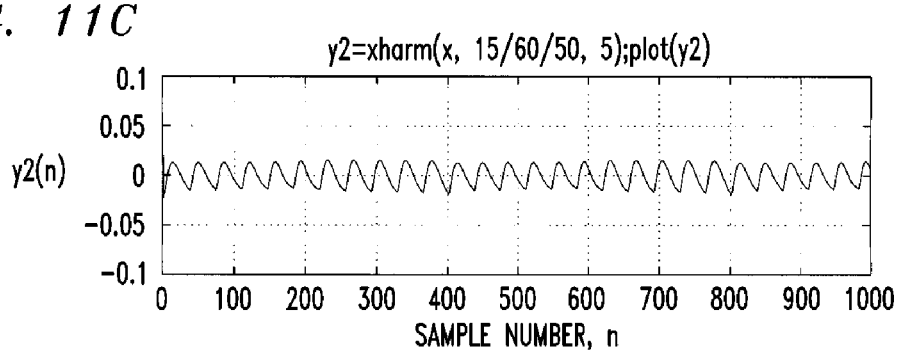
Figure 11D:
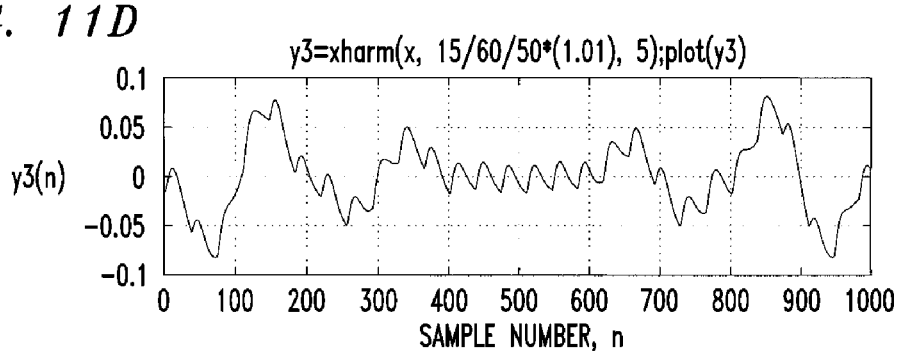
Figure 12A:
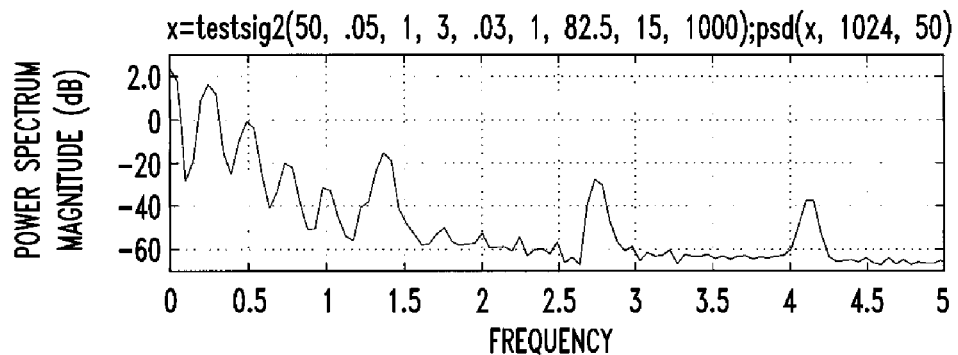
FIGS. 12A-D are plots of the power spectra of the respective signals of FIGS. 11A-D.
Figure 12B:
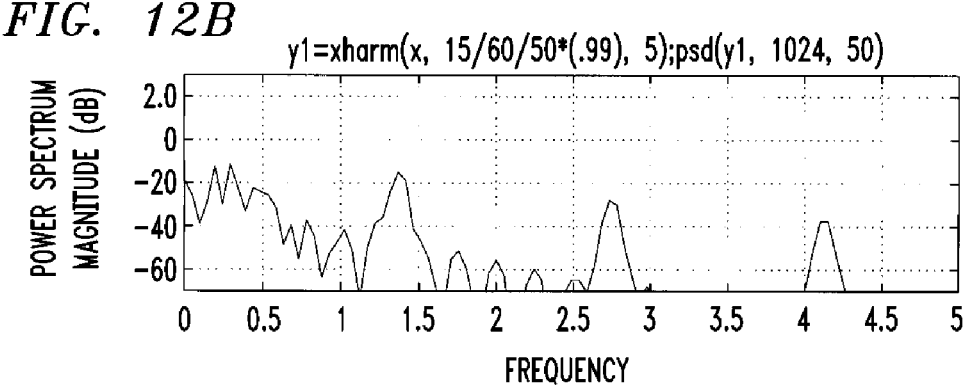
Figure 12C:
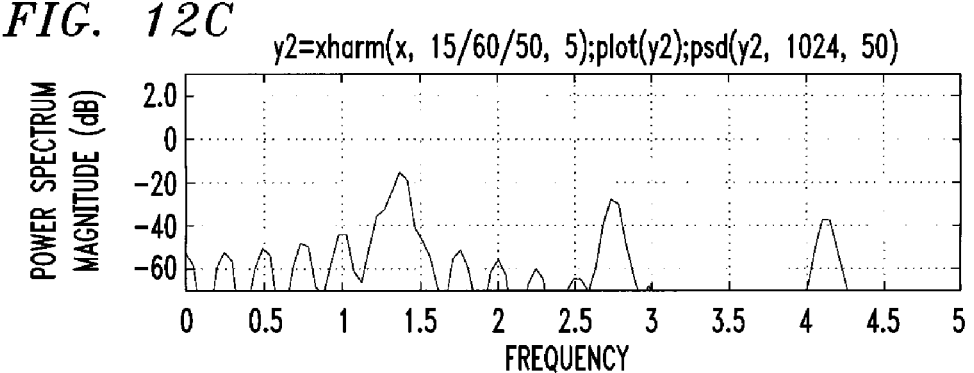
Figure 12D:
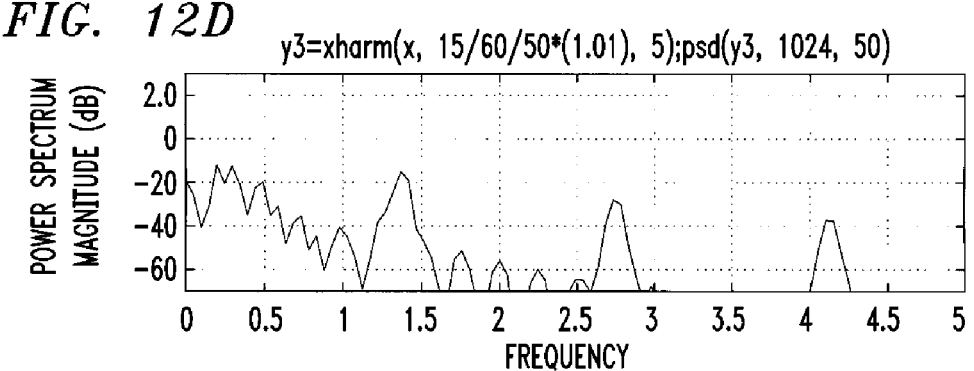

FIGS. 11A-D show how the harmonic canceller output varies with the estimated respiration frequency. FIG. 11A shows the same test signal described above, FIGS. 11B-D respectively show the output signal for −1%, 0% and +1% error (14.85, 15, 15.15 bpm) in the fundamental frequency estimate.

FIGS. 12A-D show the associated power spectra of the respective signals of FIGS. 11A-D. As can be seen, a 1% error in the estimated respiration frequency causes the fundamental suppression to rise to about the −30 dB level relative to the uncanceled fundamental. Actually, the power spectral density somewhat exaggerates the suppression in this case because the output signal is highly nonstationary and the default (Hann) window reduces the signal at its highest point. A measurement of the unwindowed MSE reduction shows about −20 dB, which closely agrees with the −20.8 dB level calculated above.

In FIG. 8, the estimated respiration rate was 14.8296 bpm, as determined from the power spectrum using three-point quadratic peak interpolation. This is close to the 1% error level examined above, so similar effects are expected. The estimate refinement technique described above was applied in this case, using a ±6% perturbation (consistent with an expected error level of 2%), and resulted in a refined estimate of 15.0211 bpm, which is close to the actual 15 bpm rate.

Thus, it is apparent that the harmonic canceller is effective in removing the respiration component of the test signal, provided that its fundamental frequency can be sufficiently well estimated. The performance with actual measured signals will now be described.

VI. EXPERIMENTAL RESULTS

A. Equipment Description and Setup

Figure 13:
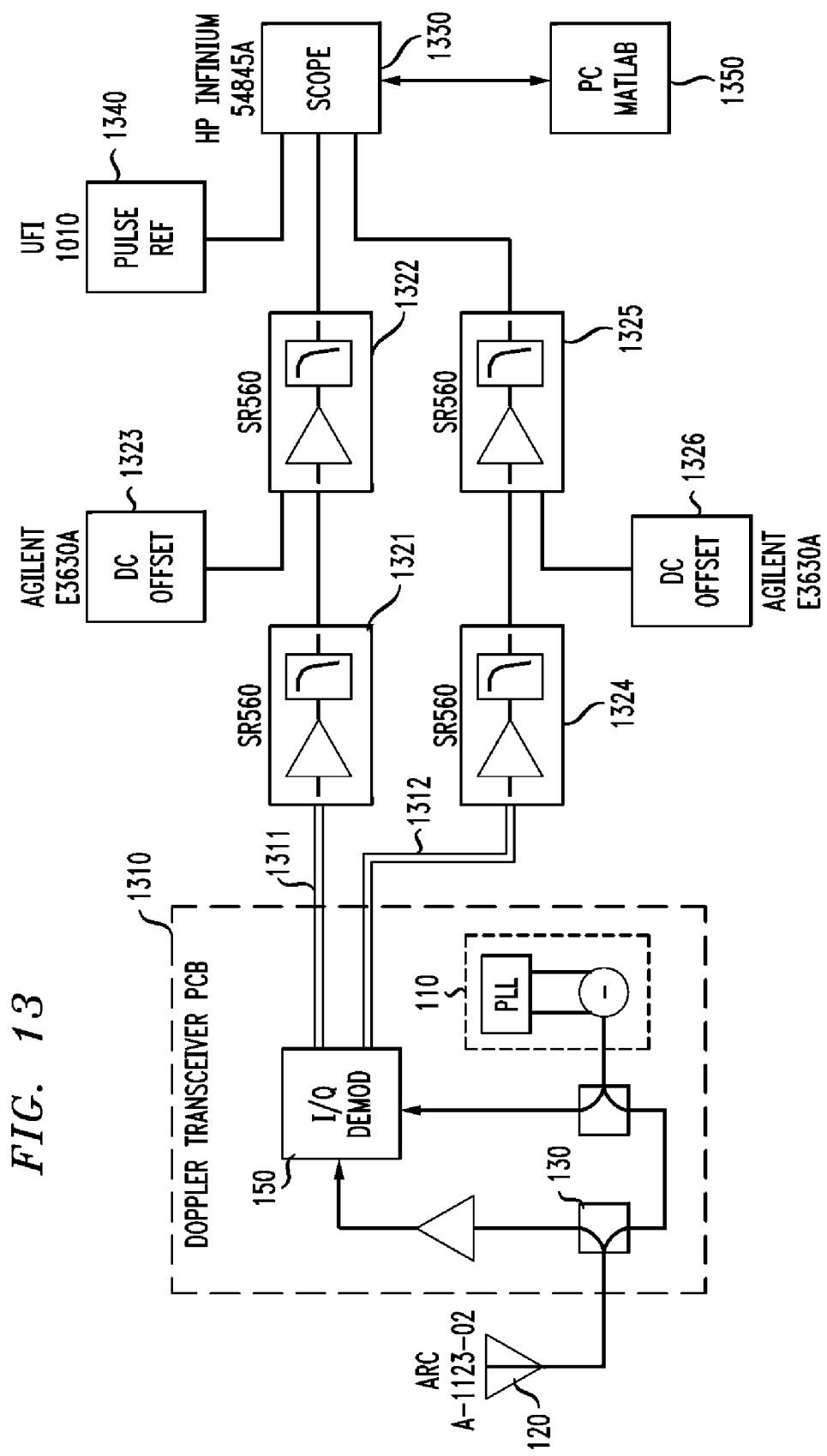
FIG. 13 is a block diagram of an experimental apparatus.

FIG. 13 shows a block diagram of the experimental apparatus. The Doppler radar setup is configured by employing a Doppler transceiver printed circuit board (PCB) 1310 having balanced I and Q output signal ports 1311, 1312. The I and Q signals are each processed in a separate chain. The following description details the I chain, which is identical to the Q chain.

The balanced I signal from PCB (IN and IP) is fed into the balanced A and B input ports of a first preamplifier (preamp)/filter 1321, e.g., one commercially available from Stanford Research Systems of Sunnyvale, Calif., as part no. SR560. The first preamp/filter 1321 not only provides amplification and filtering, but also converts the balanced input signal to a single-ended 50-ohm output (a 600-ohm output is also provided, but not used). The output of the first preamp/filter 1321 is then connected to the balanced A input of a second preamp/filter 1322. The other balanced input (B) is connected to a DC power supply 1323 that is employed to correct the DC offset of the I signal. The single-ended 50-ohm output of the second preamp/filter 1322 is then connected to one of the input ports of an oscilloscope 1330, which may be an Infinium oscilloscope commercially available from the Hewlett-Packard Company of Palo Alto, Calif. An output of the oscilloscope 1330 is connected to a personal computer (PC) 1350 running mathematical analysis software, e.g., Matlab, which is commercially available from The MathWorks of Natick, Mass.

As mentioned previously, the Q chain is the same (containing a first preamp/filter 1324, a second preamp/filter 1325 and a DC power supply 1326) and is terminated into another one of the input ports of the oscilloscope 1330. Another input to the oscilloscope 1330 comes from a piezoelectric finger pulse transducer 1340 (e.g., a Model 1010 piezoelectric pulse plethysmograph commercially available from UFI of Morro Bay, Calif.), which may be employed as a reference in the experiments described below. The input ports of the oscilloscope 1330 are all set to 50-ohms.

Lastly, the antenna 120 (e.g., an ARC A-1123-02, 19 dBi antenna, commercially available from ARC Wireless Solutions, Inc., of Wheat Ridge, Colo.) is hooked up via a 50-ohm cable to the antenna port of the PCB 1310. The antenna 120 is placed approximately at chest level on the edge of a bench pointing directly at the subject.

B. Methodology

For all experiments, the first- and second-stage preamp/filters 1321, 1322, 1324, 1325 were set at LP (lowpass), DC coupling, 12 dB/octave, and 10 Hz cutoff frequency. In addition, the first preamp/filters 1321, 1324 were set to the low-noise mode (for least contamination of low-level inputs) and the second preamp/filters 1322, 1325 to high-dynamic-reserve mode (to best accommodate high-level transients without saturating). The Table, below, shows the other equipment settings that were employed in the experiments.

TABLE

Equipment Settings for Experimental System

| Settings | Experiments 1 & 2 | Experiment 3 | Experiment 4 |
|---|---|---|---|
| SR560 gain | | | |
| 1st Stage | 5 | 5 | 5 |
| 2nd Stage | 10 | 5 | 5 |
| Overall | 50 | 25 | 25 |
| DC Offset | | | |
| I | 3.09 V | −0.98 V | −0.98 V |
| Q | 1.39 V | −2.57 V | −2.57 V |
| HP Infinium | | | |
| I/Q | 200 mV/div | 500 mV/div | 1 V/div |
| R | 100 mV/div | 100 mV/div | 100 mV/div |
| T | 2 s/div | 2 s/div | 2 s/div |

Once everything is configured, the following initialization may then be performed. Without a subject in front of the antenna 120, both the I and Q offset power supplies may be varied one at a time until the oscilloscope 1330 reads a steady 0 V on each trace. This stop is done mainly to keep the varying signals within the viewing scale chosen, so as not to saturate the captured signals.

Following the initialization, the subject is introduced into the antenna 120 field of view. For most of the static experiments, the subject is seated on a chair at a 1-m distance from the antenna 120. For the dynamic experiments, the subject distance varies from about 1 m to 4 m.

The oscilloscope 1330 is set on a long sweep (typically 20 s) and when the trace is complete, the oscilloscope 1330 is set to stop. The captured signals are then one-by-one exported as .csv files, which are in turn converted to a single formatted ASCII test file (four columns [t i q r] that the Matlab routines can read.

C. Experiment 1

Subject Stationary at 1 m from Antenna, Remaining Still and Holding Breath

Figure 14A:
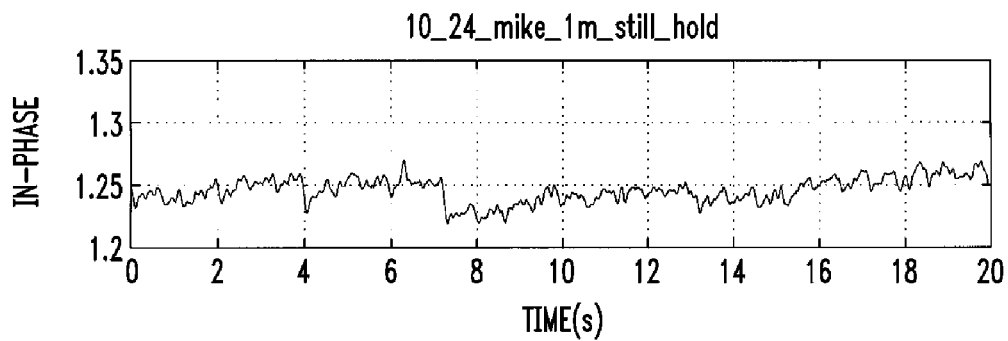
FIGS. 14A-C are plots of a raw I signal (FIG. 14A), a raw Q signal (FIG. 14B) and a reference signal (FIG. 14C) for Experiment 1 under three conditions: subject stationary at 1 m from antenna, remaining still and holding breath.
Figure 14B:
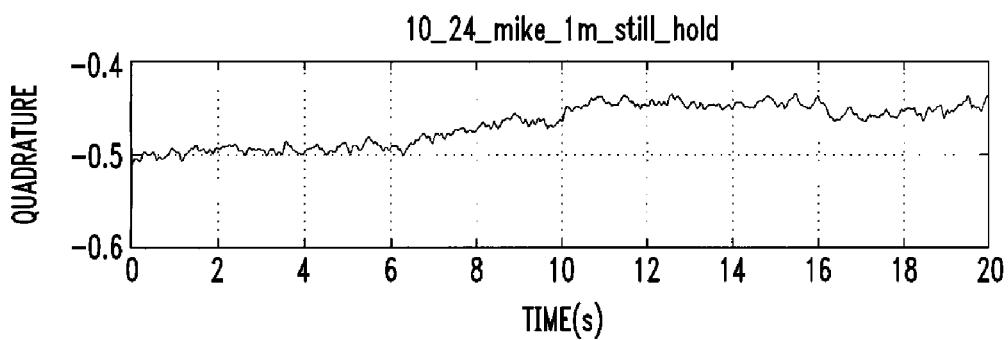
Figure 14C:
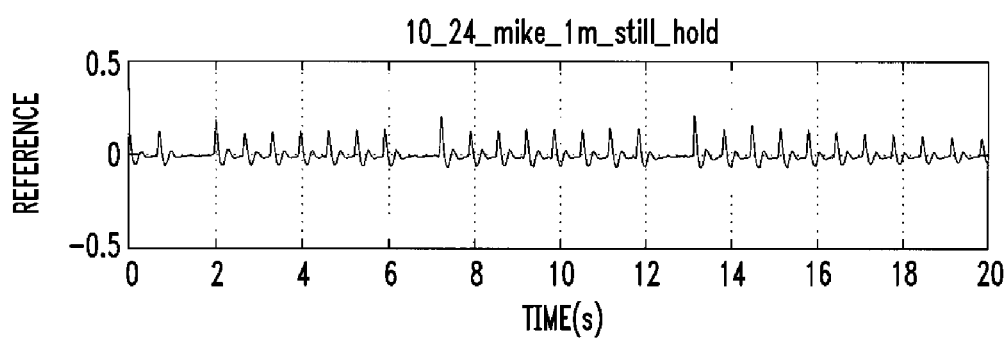
Figure 14D:
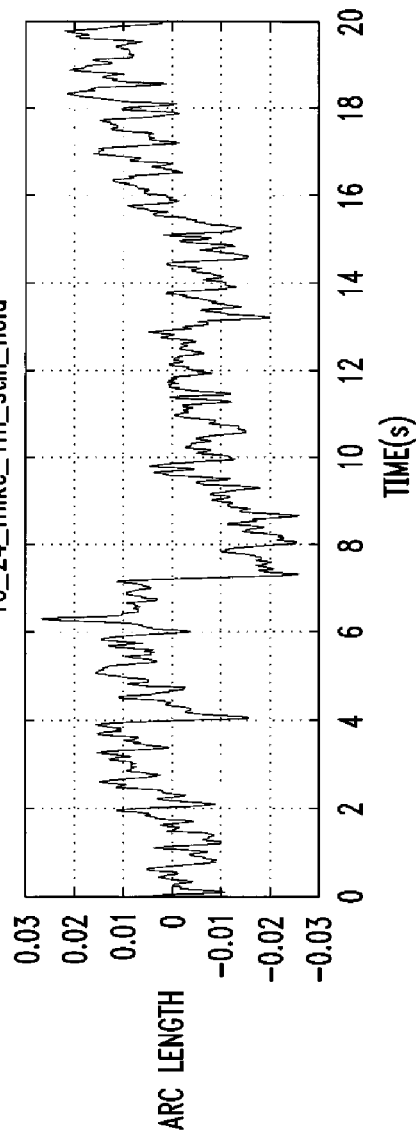
FIG. 14D is a plot of the arc length signal relating to the I and Q signals of FIGS. 14A and 14B, respectively.
Figure 14E:
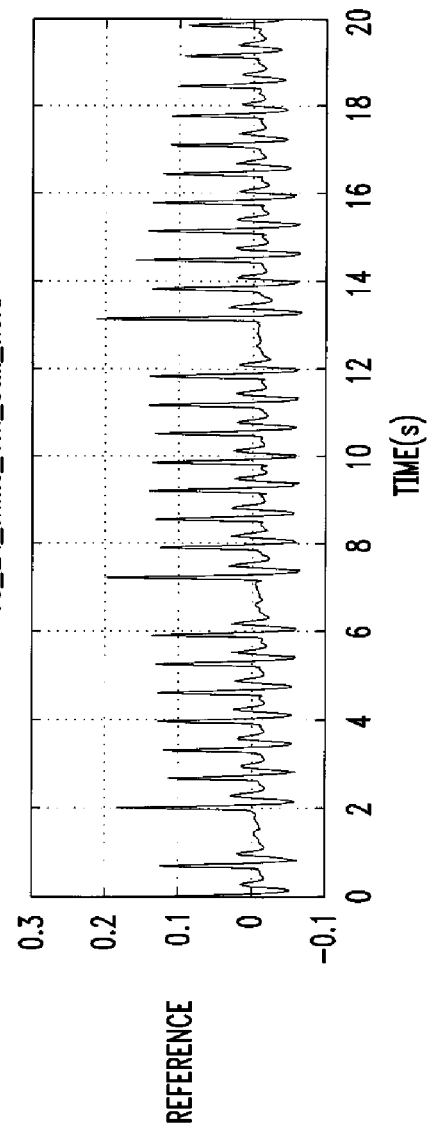
FIG. 14E is a plot of the arc length signal relating to the reference signal of FIG. 14C.

In the first experiment, the subject is seated at a distance of 1 m from the antenna and holds his breath so that no interference from respiration occurs. FIGS. 14A-C show plots of the raw I and Q signals (FIGS. 14A and B), along with the reference pulse signal (FIG. 14C). The heartbeat signal is apparent, which is strongly correlated with the reference signal. FIG. 14D shows the arc-length signal calculated from Equation (4), which optimally combines the I and Q signals.

Figure 14F:
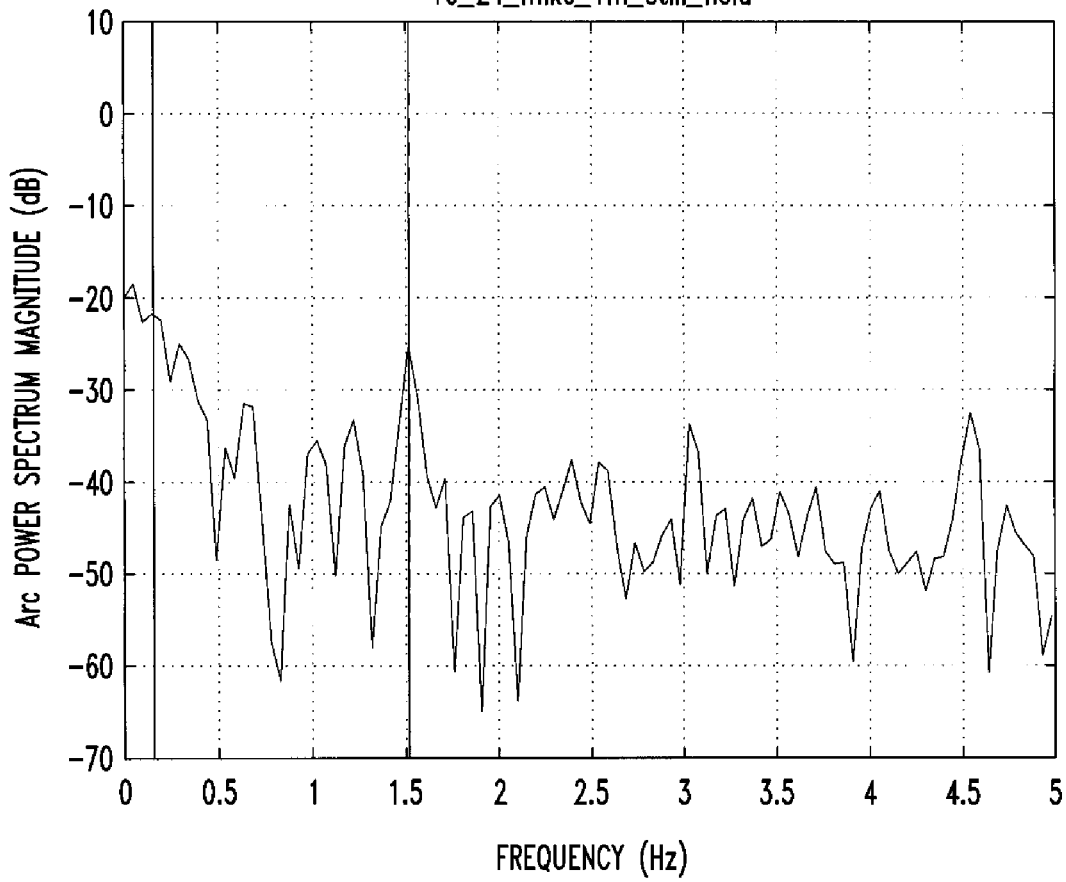
FIG. 14F is a plot of the power spectrum of the arc length signal of FIG. 14D, also showing the estimated respiration and heart rates (solid vertical lines) as well as the actual heart rate (dashed vertical line, obscured in this case)

The spectrum of the arc-length signal is plotted in FIG. 14F, which also displays the estimated respiration and heart rates (solid vertical lines), as well as the actual heart rate (dashed vertical line) from the reference signal. (In this case, the estimated respiration rate is probably spurious since the subject is purposely holding his breath. Also, the dashed line is obscured in this case since the estimated heart rate is so close to the actual heart rate.) The numerical value of the estimated respiration (spurious in this case) and heart rates, along with the actual heart rate are displayed in FIG. 14F. The estimated heart rate is 90.9324 bpm, which is virtually identical to the actual displayed heart rate of 91.0008 bpm. These results are typical under idealized conditions, so near-perfect heart-rate estimates may be obtained. Experiment 2 is then undertaken to assess the effects of respiration when the subject is breathing normally.

Experiment 2

Subject Stationary at 1 m from Antenna, Remaining Still and Breathing Regularly

Figure 15D:
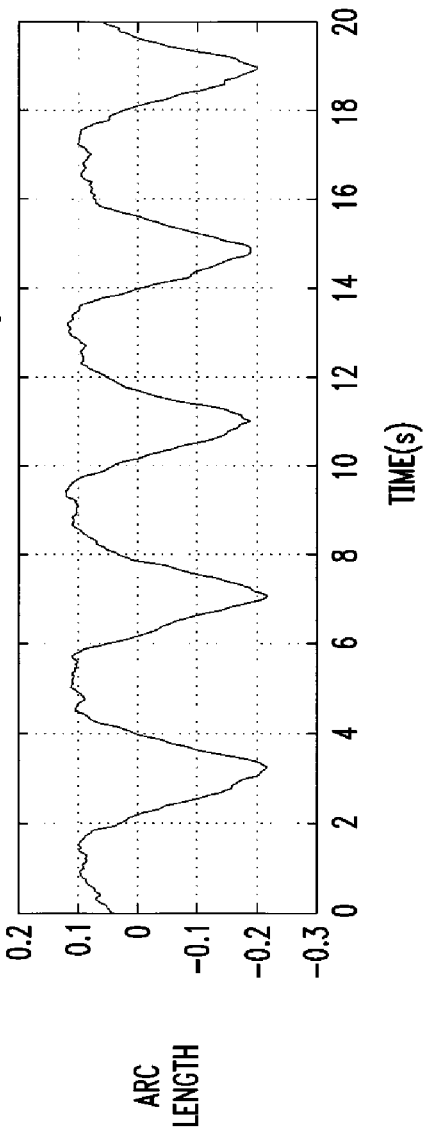
FIG. 15D is a plot of the arc length signal relating to the I and Q signals of FIGS. 15A and 15B, respectively.
Figure 15E:
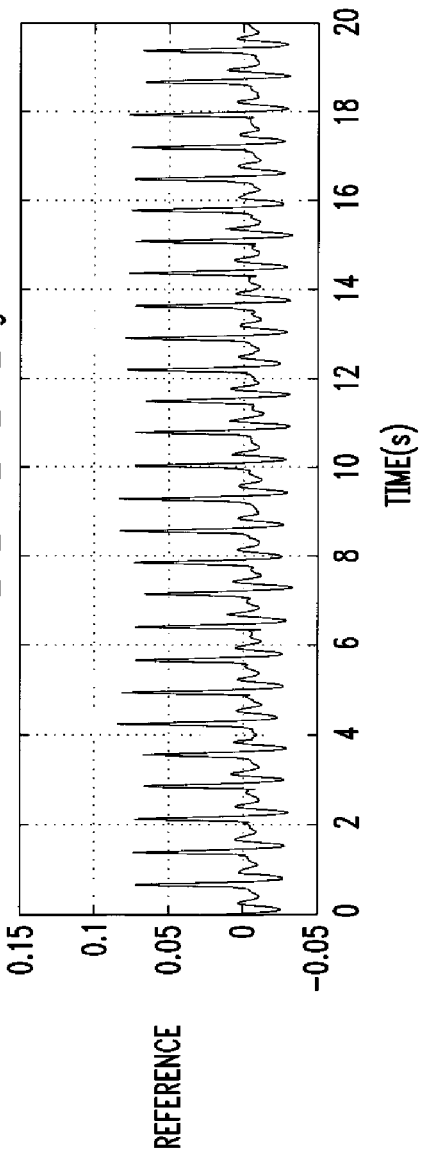
FIG. 15E is a plot of the arc length signal relating to the reference signal of FIG. 15C.

In Experiment 2, the same subject is seated in the same position, but is now breathing in a regular manner. FIGS. 15A-F display the same information as FIGS. 14A-F for Experiment 1. Comparing the two, FIG. 15A-C show that the respiration component is now dominant and the heartbeat component is difficult to see. The respiration rate is roughly 5 cycles over 20 s, or 15 bpm. Comparing FIG. 15D with FIG. 14D shows that the peak-to-peak heartbeat component in the former is roughly 0.015 V as compared to a peak-to-peak respiration component of about 0.3 V in the latter, i.e., a ratio of 1:20 or 26 dB. FIG. 15C can also be compared to the test signal of FIG. 7C, showing much similarity.

Figure 15F:
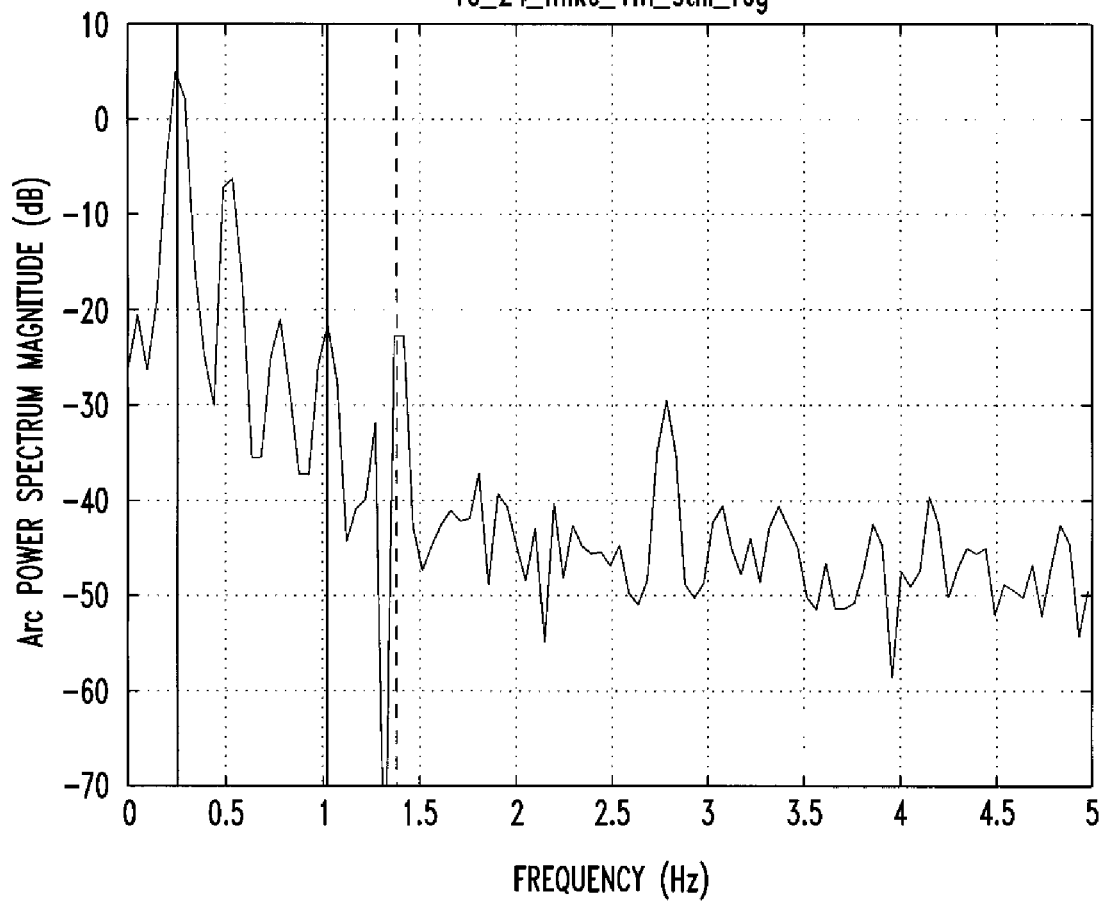
FIG. 15F is a plot of the power spectrum of the arc length signal of FIG. 15D, also showing the estimated respiration and heart rates (solid vertical lines) as well as the actual heart rate (dashed vertical line)

As compared to FIG. 14F, the power spectrum of FIG. 15F is now cluttered with many respiration harmonics, making it difficult to decide which peak corresponds to the heartbeat component. Indeed, the heart-rate estimation algorithm (see description in Section V-B) fails in this case, as the estimated heart rate is captured by the fourth harmonic of the respiration. However, the respiration rate estimate of 15.1083 bpm (0.2518 Hz) seems to be in line with the observed period in FIG. 15F, and this will be employed next to apply the harmonic cancellation technique.

Figure 16A:
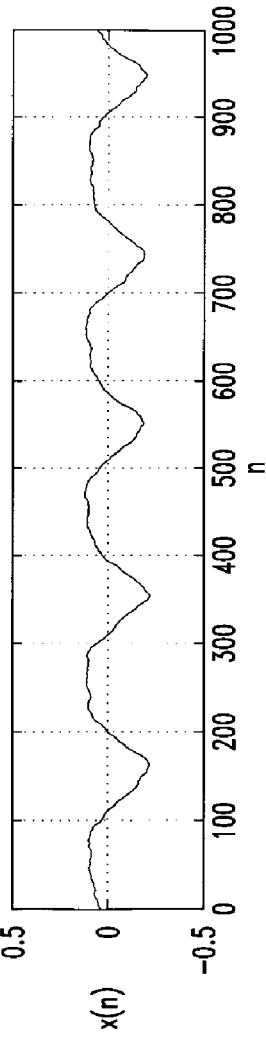
FIGS. 16A-C are plots of an input signal (FIG. 16A), an enhanced heartbeat output signal (FIG. 16B) and an enhanced respiration signal (FIG. 16C) showing cancellation of the first $L=5$ respiration harmonics using the arc length signals of FIGS. 15D and E as an input and the respiration rate estimate of 15.1083 bpm from FIG. 15E.
Figure 16B:
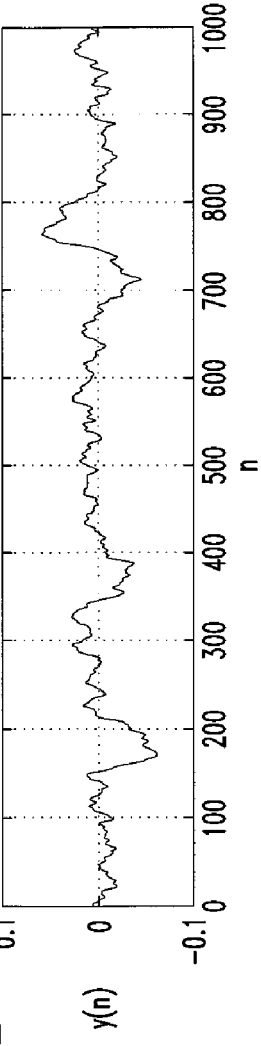
Figure 16C:
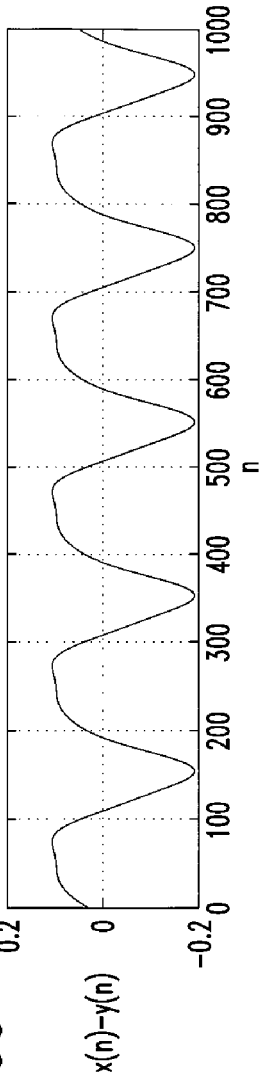
Figure 16D:
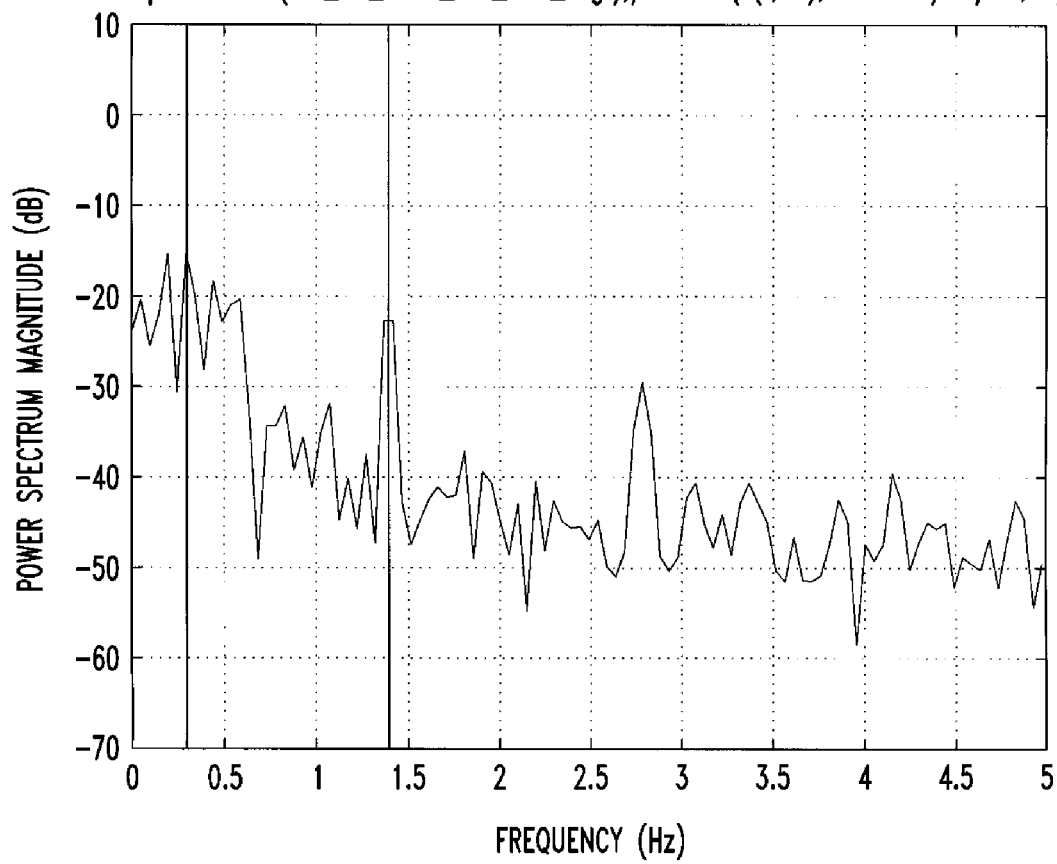
FIG. 16D is a plot of the power spectrum of the enhanced heartbeat output signal of FIG. 16B.

Following the same procedure set forth in Section V-C above, the harmonic cancellation technique of Section IV is applied to the above data. Using the estimation respiration rate of 15.1083 bpm that appears FIG. 15F and canceling the first five harmonics, FIGS. 16A-C show that most of the respiration component has been successfully removed. Moreover, the 83.5317 bmp estimated heart rate displayed in FIG. 16D is now within 1% of the true 82.8988 bpm rate shown in FIG. 15F. (The estimated respiration rate is irrelevant in this case because the respiration component has been canceled.)

A refined respiration rate estimate was calculated as 15.2261 bpm by applying the technique of Section IV using a ±6% perturbation (consistent with an expected error level of 2%), which is within 1% of the initial estimate of 15.1083 bpm, and hence is good for about 20 dB of cancellation, according to theory of Section IV and described in Section V-C. Therefore, in this particular example, refinement is not necessary, since the initial estimate is close enough.

E. Experiment 3

Subject Reciprocating at 1 m from Antenna and Breathing Regularly

Experiment 3 introduces movement for the first time. Now the same subject is standing 1 m in front of the antenna, and slowly takes one step forward, one step back, one step back, and one step forward, with the same foot moving in both directions, the other foot immobile, and a slight pause after each move. The subject repeats this four-move reciprocating cycle about 3½ times over the 20 s data collection period. The I/Q and reference data are plotted in FIG. 17A-C. In comparison with the still data of Experiments 1 and 2 shown in FIGS. 14A-C and 15A-C, large sinusoidal variations corresponding to the motion over many λ/2 (6.25 cm at 2.4 GHz) Doppler cycles are apparent. For this example, about nine cycles exist from trough to peak and from peak to trough, corresponding to a peak-to-peak motion of 9×6.25 cm≈0.56 m. Thus, considering the nominal 1 m distance to the antenna, the range varies from about 0.72 m to 1.28 m, i.e., a max/min ratio of about 1.8.

In this case, the arc-length transformation is not appropriate due to the large-scale motion, so this data should be examined from a different perspective. FIG. 17D plots the unwrapped phase in terms of Doppler cycles. This is in agreement with the previous observation that the peak-to-peak motion consists of about nine cycles, i.e., approximately 0.56 m.

Figure 17F:
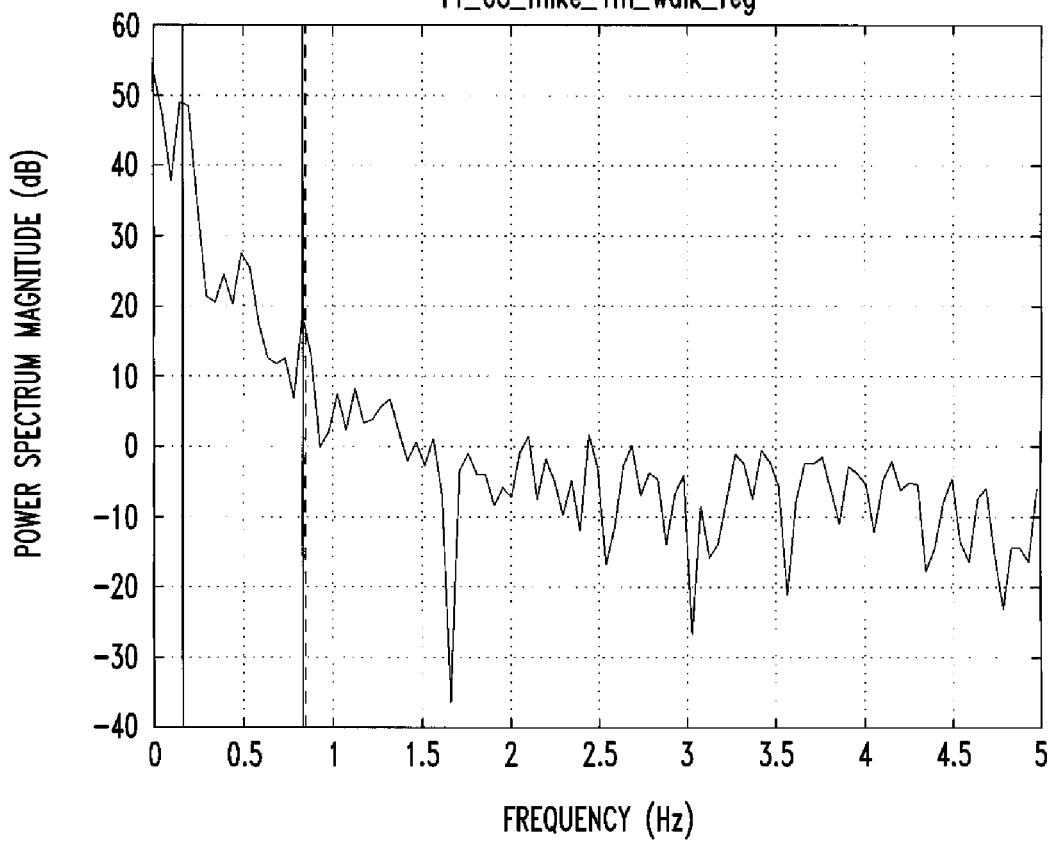
FIG. 17F is a plot of the power spectrum of the unwrapped phase arctangent of FIG. 17D, also showing the estimated respiration and heart rates (solid vertical lines) as well as the actual heart rate (dashed vertical line)

The arc-length power spectrum, employed in FIGS. 14F and 15F would also not be appropriate here because of the large-scale motion. Instead, FIG. 17F plots the power spectrum of the unwrapped phase arctangent. In this case, the estimated respiration rate of 9.82236 bpm (0.1637 Hz) that appears is clearly in error because its period of $$\frac{1}{0.1637} = 6.1085$$

s is instead identified as the period of the reciprocating motion in FIG. 17D. Likewise, the estimated heart rate of 49.9788 bpm (0.8330 Hz) is erroneous, having been captured as the fifth harmonic of the periodic motion. By coincidence the "true" heart rate is also in error here because of some problems with extraneous noise pickup in the reference channel. However, the reference time waveform in FIG. 17D indicates that the true heart rate is about 90 bpm (1.5 Hz) in this case, which cannot be reliably detected in FIG. 17F.

Figure 18:
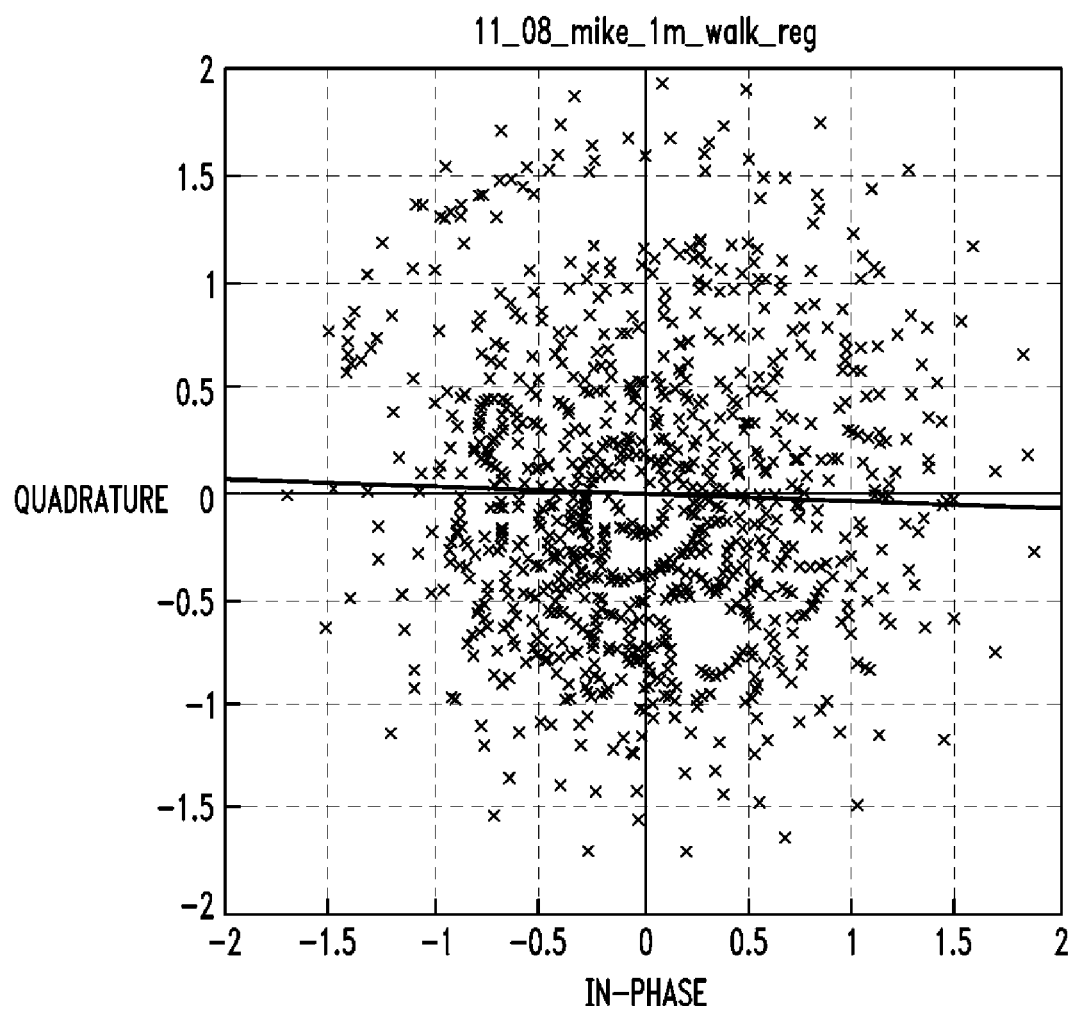
FIG. 18 is a plot of I and Q components of Experiment 3 employed for absolute distance calibration.

Experiment 3 also enables absolute motion calibration of the system. FIG. 18 plots the relationship between the I and Q components. (The skewed line in FIG. 18 is a linear regression fit, which is only relevant over small arcs and so is not useful here.) It is apparent that the data rotates one cycle for each λ/2 (6.25 cm) of motion, and also the amplitude peaks and ebbs as the subject is closer to and then further away from the antenna. The diameter of the circles traced out varies between about 0.6 V and 3 V, i.e., a voltage ratio of about 5:1. In the far field, the voltage would be expected to be inversely proportional to range, which would imply a range ratio of about 5. However, this is significantly higher than the 1.8 ratio calculated above by counting cycles. The disparity may be due to antenna near-field effects, since at times the subject may be closer than 1 m from the antenna, or random scattering effects as the subject's aspect angle changes slightly during forward and backward motion.

In any case, the observed voltage may be employed to calibrate the system by associating the harmonic mean diameter of $$\frac{1}{\left(\frac{1}{0.6} + \frac{1}{3}\right)} = 0.5$$

V with the nominal 1 m range. (Note that absolute phase cannot be employed for calibration in the non-moving scenario because small arcs have no easily obtainable absolute reference point—see FIG. 2.) Therefore, according to the description in Section III-B, 0.5 V would correspond to an arc length of λ/2 over π, which equals 1.99 cm at 2.4 GHz, i.e., about 4 cm/V. The Table shows that the overall gain for Experiments 1 and 2 was twice the gain for Experiment 3, so for Experiments 1 and 2, the calibration would be 2 cm/V. Accordingly, the 0.015 V peak-to-peak heartbeat signal previously estimated from FIG. 14D corresponds to 2×0.015=0.03 cm, or 0.3 mm peak-to-peak chest-wall motion, which is within the range of expected values. Likewise, the 0.3 V peak-to-peak respiration signal previously estimated from FIG. 15D corresponds to 2×0.3=0.6 cm=6 mm peak-to-peak chest-wall motion, which is again within range of expected values.

Experiment 4

Subject Slowly Walking Toward Antenna and Breathing Regularly

Figure 19A:
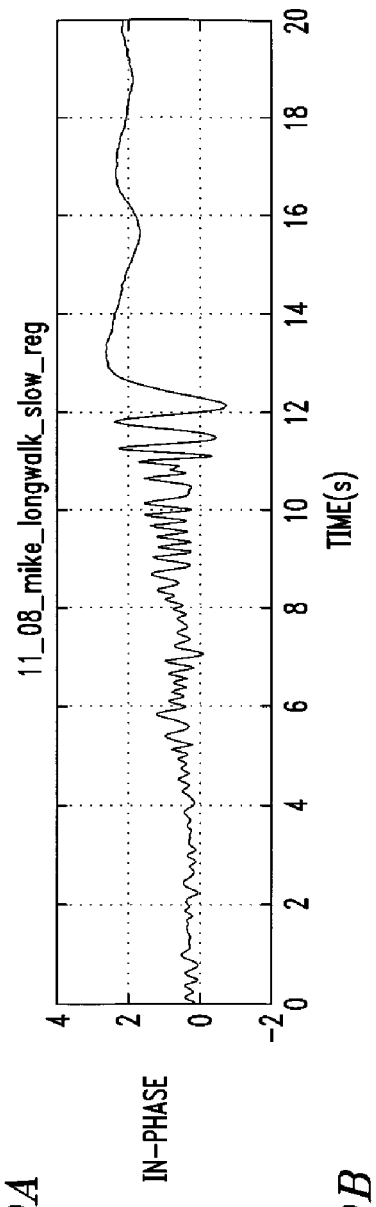
FIGS. 19A-C are plots of a raw I signal (FIG. 19A), a raw Q signal (FIG. 19B) and a reference signal (FIG. 19C) for Experiment 4 over an entire 20-s interval under three conditions: subject slowly walking toward antenna and breathing regularly.
Figure 19B:
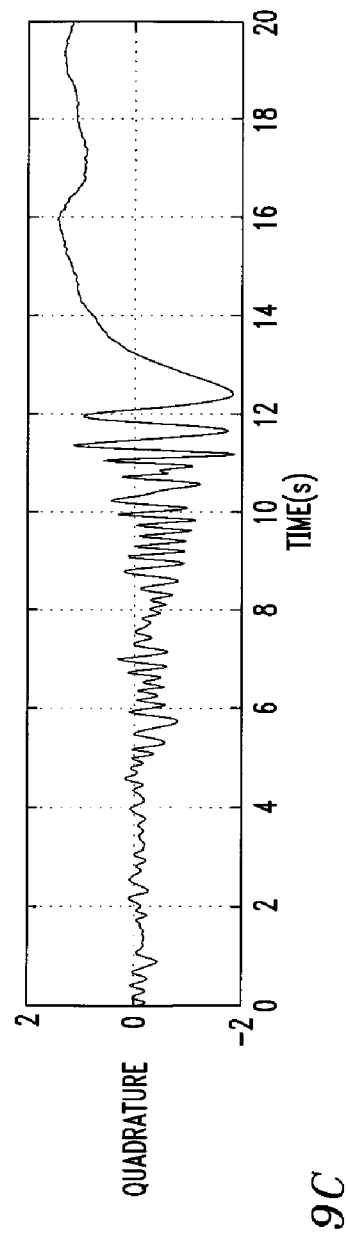
Figure 19C:
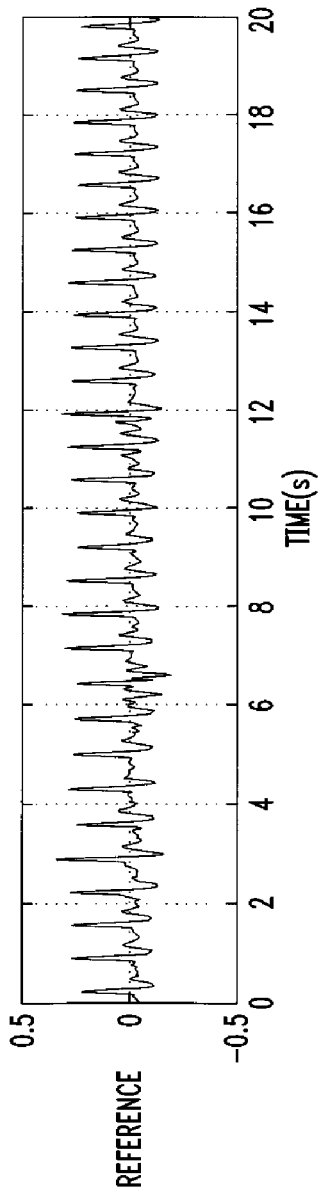

Experiment 4 demonstrates the performance when the same subject is slowly walking towards the antenna, starting at a distance of about 5 m and ending at about 1 m ("long-walk"). FIGS. 19A-C shows the raw I/Q data, in which the amplitude of the Doppler cycles slowly builds up until the subject reaches the 1 m distance at about 12 s. The segment from about 10 s to 12 s roughly corresponds to similar 2 s segments in FIG. 17A-C. Since the subject covers the entire 4 m distance in about 12 s, the average velocity of the subject is about $$\frac{4}{12} = \frac{1}{3} \text{m/s}.$$

Over the first 5 s, the signal is too weak to get reliable phase measurements. Accordingly, the data is windowed from 5 s to 12 s. FIGS. 20A-C show the resulting raw I/Q data and the reference signal over this 7 s interval, in which the amplitude of the Doppler cycles slowly builds up until the subject reaches the 1 m distance.

Figure 20D:
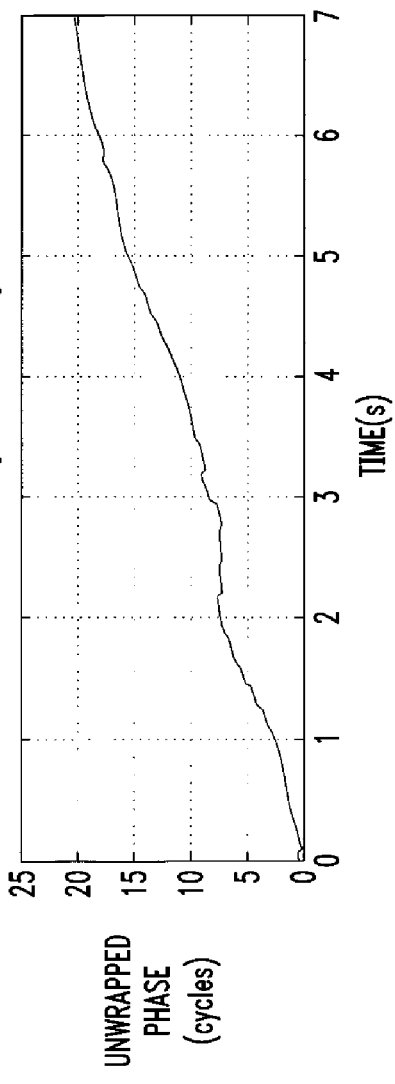
FIG. 20D is a plot of the unwrapped phase arctangent of the I and Q signals of FIGS. 20A and 20B.
Figure 20E:
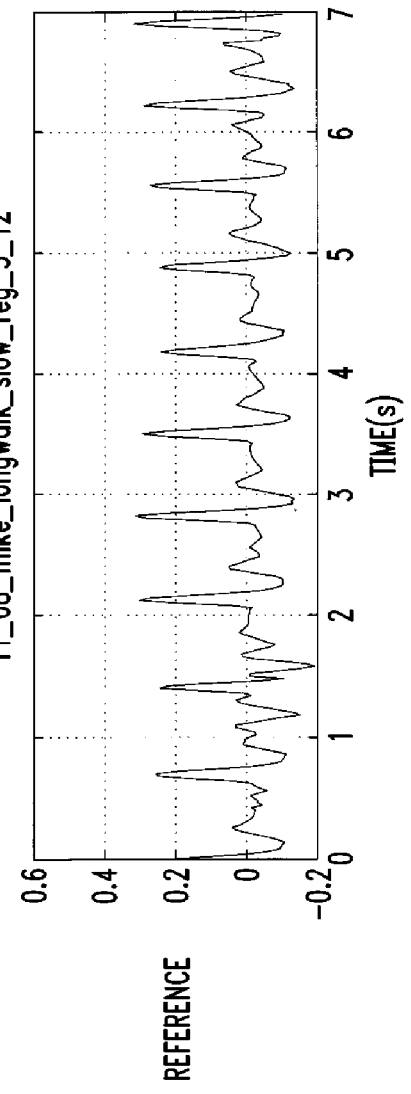
FIG. 20E is a plot of the arc length signal relating to the reference signal of FIG. 20C.

FIG. 20D plots the phase. Here, due to the apparent baseline drift in FIG. 20A-C from about 2 s to 3 s, some Doppler cycles are missing, which results in a flat spot in the phase plot. Over the last two seconds, the subject is slowing down as the 1 m distance is reached. Fitting a straight line to the interval from 3 s to 5 s shows about eight Doppler cycles, i.e., 8×6.25 cm=50 cm, over 2 s for a velocity of 0.25 m/s, being roughly consistent with the previously estimated overall velocity of ⅓ m/s.

Figure 20F:
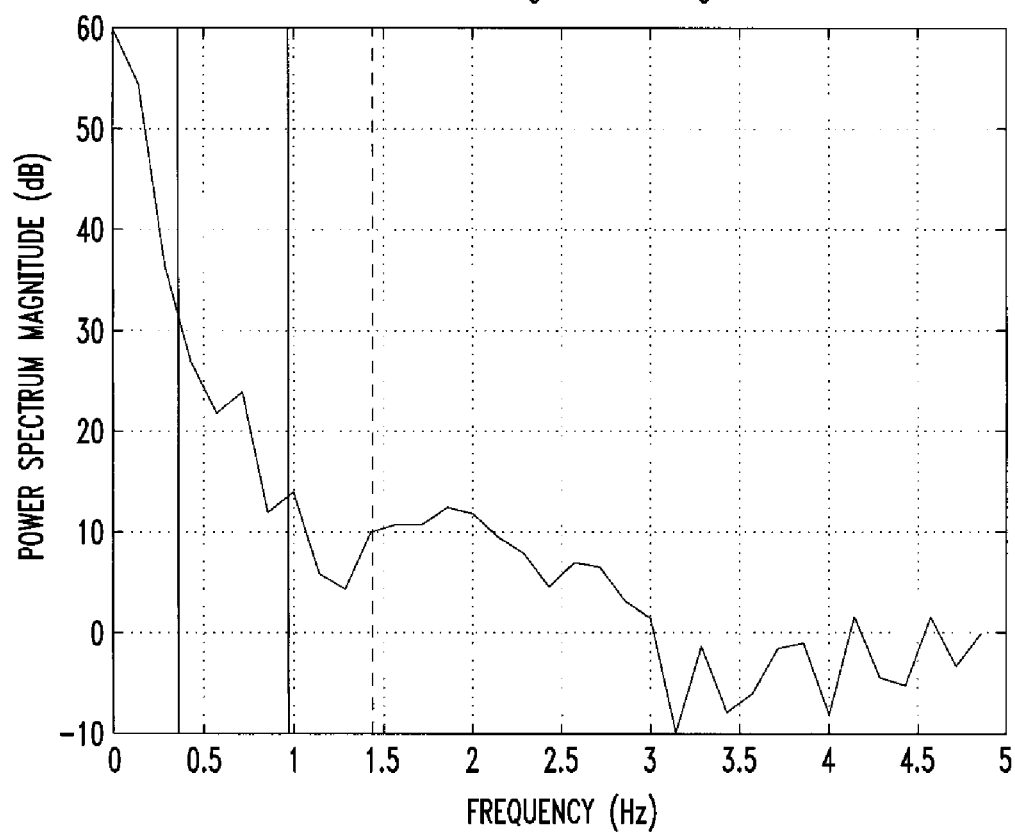
FIG. 20F is a diagram of the power spectrum of unwrapped phase arctangent of FIG. 20D, also showing the estimated respiration and heart rates (solid vertical lines) as well as the actual heart rate (dashed vertical line)
Figure 21:
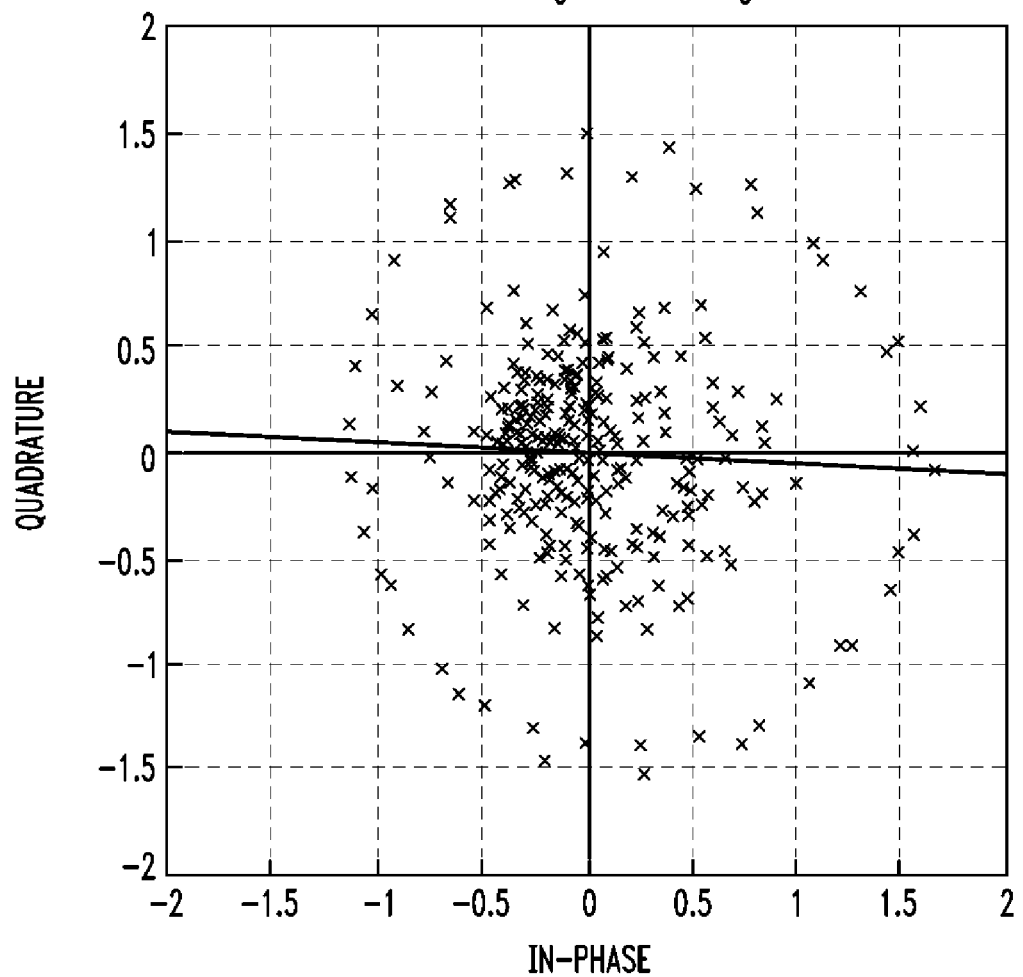
FIG. 21 is a plot of I and Q components of Experiment 4 employed for absolute distance calibration.

The unwrapped phase arctangent spectrum is displayed in FIG. 20F. Here again, as with the data in FIG. 17F, it is difficult to extract any kind of reliable estimate of either respiration rate or heart rate. In these cases, the dynamics of motion seem to overwhelm the small variations that respiration rate or heart rate cause. For completeness, FIG. 21 also plots I/Q data, where the spiral pattern that was evident in FIG. 18 is seen again.

FIG. 22 is a flow diagram of one embodiment of a method of CP signal processing. The method begins in a start step 2210 by calibrating a Doppler radar. In a step 2220, at least one radar output signal that represents a reflected Doppler radar signal is received from the Doppler radar. In a step 2230, the at least one radar output signal is converted to digital form with an ADC. In a step 2240, an arc-length CP signal is produced from the at least one radar output signal. In a step 2250, a respiration fundamental frequency estimate is employed to extract a heart rate signal from the arc-length cardiopulmonary signal. In a step 2260, a respiration signal is extracted from the arc-length cardiopulmonary signal. In a step 2270, the heart rate signal and the respiration signal are provided at an output. The method ends in an end step 2280.

VII. CONCLUSIONS

Disclosed herein are signal processing systems and methods for Doppler radar CP sensing that enable estimation of respiration and heart rate from measurements of chest-wall dynamic motion. A generic model was formulated in the complex plane to visualize production of the desired chest-wall displacement signal as well as possible interfering signals, and various signal processing routines were developed based on that model. A harmonic cancellation technique was developed for reducing the large respiration component so that the weaker heartbeat signal can be reliably extracted, thereby greatly improving the accuracy of heart rate estimation. The signal processing techniques were studied and evaluated using both a simulated test signal and experiments involving actual data collected from a laboratory setup using a live subject. The results of this study and evaluation show that reliable respiration and heart rate estimation is possible when the subject is seated at rest. However, with dynamic motion of the subject, as when walking or jogging, the relatively large body motion can overwhelm the relatively small respiration and heartbeat signals, making reliable estimation of rates difficult.

Those skilled in the art to which the invention relates will appreciate that other and further additions, deletions, substitutions and modifications may be made to the described embodiments without departing from the scope of the invention.

What is claimed is:

1. A Doppler radar signal processing system, comprising:
an input configured to receive at least one radar output signal representing a reflected Doppler radar signal;
signal processing circuitry coupled to said input and configured to produce an arc-length cardiopulmonary signal from said at least one radar output signal and employ a respiration fundamental frequency estimate to extract a heart rate signal from said arc-length cardiopulmonary signal; and
an output coupled to said signal processing circuitry and configured to provide said heart rate signal.

2. The system as recited in claim 1 wherein said signal processing circuitry is further configured to extract a respiration signal from said arc-length cardiopulmonary signal and said output is further configured to provide said respiration signal.

3. The system as recited in claim 1 wherein said at least one radar output signal includes an in-phase signal and a quadrature signal.

4. The system as recited in claim 3 wherein said signal processing circuitry includes in-phase and quadrature analog-to-digital converters configured to convert said in-phase signal and said quadrature signals, respectively, to digital form.

5. The system as recited in claim 4 wherein said analog-to-digital converters are DC-coupled.

6. The system as recited in claim 1 wherein said signal processing circuitry is further configured to perform a block-averaged mean subtraction on said at least one radar output signal.

7. The system as recited in claim 1 wherein said signal processing circuitry is further configured to produce a harmonic signal representing at least one harmonic of said respiration fundamental frequency estimate and employ said at least one harmonic signal to extract said heart rate signal from said arc-length cardiopulmonary signal.

8. A method of CP signal processing, comprising:
calibrating a Doppler radar;
receiving at least one radar output signal from said Doppler radar representing a reflected Doppler radar signal;
producing an arc-length cardiopulmonary signal from said at least one radar output signal;
employing a respiration fundamental frequency estimate to extract a heart rate signal from said arc-length cardiopulmonary signal; and
providing said heart rate signal at an output.

9. The method as recited in claim 8 further comprising extracting a respiration signal from said arc-length cardiopulmonary signal, said providing including providing said respiration signal at said output.

10. The method as recited in claim 8 wherein said at least one radar output signal includes an in-phase signal and a quadrature signal.

11. The method as recited in claim 10 further comprising converting said in-phase signal and said quadrature signals to digital form with analog-to-digital converters.

12. The method as recited in claim 11 wherein said analog-to-digital converters are DC-coupled.

13. The method as recited in claim 8 further comprising performing a block-averaged mean subtraction on said at least one radar output signal.

14. The method as recited in claim 8 further comprising:
producing a harmonic signal representing at least one harmonic of said respiration fundamental frequency estimate; and
employing said at least one harmonic signal to extract said heart rate signal from said arc-length cardiopulmonary signal.

15. A Doppler radar, comprising:
Doppler radar circuitry configured to transmit a Doppler radar signal, receive and demodulate a reflected Doppler radar signal and produce in-phase and quadrature radar output signals representing said reflected Doppler radar signal;
signal processing circuitry coupled to said input and configured to produce an arc-length cardiopulmonary signal from said in-phase and quadrature radar output signals and employ a respiration fundamental frequency estimate to extract a heart rate signal from said arc-length cardiopulmonary signal; and an output coupled to said signal processing circuitry and configured to provide said heart rate signal.

16. The Doppler radar as recited in claim 15 wherein said signal processing circuitry is further configured to extract a respiration signal from said arc-length cardiopulmonary signal and said output is further configured to provide said respiration signal.

17. The Doppler radar as recited in claim 15 wherein said signal processing circuitry includes in-phase and quadrature analog-to-digital converters configured to convert said in-phase signal and said quadrature signals, respectively, to digital form.

18. The Doppler radar as recited in claim 17 wherein said analog-to-digital converters are DC-coupled.

19. The Doppler radar as recited in claim 15 wherein said signal processing circuitry is further configured to perform a block-averaged mean subtraction on said at least one radar output signal.

20. The Doppler radar as recited in claim 15 wherein said signal processing circuitry is further configured to produce a harmonic signal representing at least one harmonic of said respiration fundamental frequency estimate and employ said at least one harmonic signal to extract said heart rate signal from said arc-length cardiopulmonary signal.

* * * * *